(12) United States Patent
Stilwell et al.

(10) Patent No.: US 11,452,796 B2
(45) Date of Patent: Sep. 27, 2022

(54) CELLULAR BONE GRAFTS, AND METHODS OF MANUFACTURE AND USE

(71) Applicant: AlloSource, Centennial, CO (US)

(72) Inventors: Reginald Stilwell, Parker, CO (US); Ramasamy Sakthivel, Parker, CO (US); William Maslanik, Littleton, CO (US)

(73) Assignee: AlloSource, Centennial, CO (US)

( * ) Notice: Subject to any disclaimer, the term of this patent is extended or adjusted under 35 U.S.C. 154(b) by 25 days.

(21) Appl. No.: 16/625,457

(22) PCT Filed: Jun. 29, 2018

(86) PCT No.: PCT/US2018/040332
§ 371 (c)(1),
(2) Date: Dec. 20, 2019

(87) PCT Pub. No.: WO2019/006328
PCT Pub. Date: Jan. 3, 2019

(65) Prior Publication Data
US 2021/0146007 A1    May 20, 2021

Related U.S. Application Data

(60) Provisional application No. 62/527,628, filed on Jun. 30, 2017.

(51) Int. Cl.
*A61L 27/00* (2006.01)
*A61L 27/36* (2006.01)
(Continued)

(52) U.S. Cl.
CPC ......... *A61L 27/3608* (2013.01); *A61L 27/222* (2013.01); *A61L 27/365* (2013.01);
(Continued)

(58) Field of Classification Search
CPC ............. A61L 27/3608; A61L 27/3847; A61L 2300/414; A61L 2430/02; A61L 27/365;
(Continued)

(56) References Cited

U.S. PATENT DOCUMENTS 4,627,853 A    12/1986  Campbell et al.
5,284,655 A    2/1994   Bogdansky et al.
(Continued)

FOREIGN PATENT DOCUMENTS

WO    2008027864 A2    3/2008
WO    2012135205       10/2012
(Continued)

OTHER PUBLICATIONS

Florencio-Silva et al. (BiomMed Research International 20'5; Article ID 421746; 17 pages). (Year: 2015).*
(Continued)

*Primary Examiner* — Ernst V Arnold
(74) *Attorney, Agent, or Firm* — Kilpatrick Townsend & Stockton, LLP; Landin Boring; Jennifer Giordano-Coltart

(57) ABSTRACT

The disclosure provides bone graft materials, methods for their use and manufacture. Exemplary bone graft materials comprise combining a radiopaque component with a cancellous bone component to produce a bone graft material, wherein the cancellous bone component comprises native osteoreparative cells. Methods for treating a subject with the bone graft material are also provided.

30 Claims, 9 Drawing Sheets

(51) Int. Cl.
*A61L 27/22* (2006.01)
*A61L 27/38* (2006.01)

(52) U.S. Cl.
CPC ....... *A61L 27/3637* (2013.01); *A61L 27/3683* (2013.01); *A61L 27/3821* (2013.01); *A61L 27/3847* (2013.01); *A61L 2300/236* (2013.01); *A61L 2300/414* (2013.01); *A61L 2430/02* (2013.01); *A61L 2430/38* (2013.01)

(58) Field of Classification Search
CPC .. A61L 27/3683; A61L 27/3821; A61L 27/50; A61L 2300/236; A61L 2430/38; A61L 27/222; A61L 27/3637; A61L 2002/2835; A61L 2/28
See application file for complete search history.

(56) References Cited

U.S. PATENT DOCUMENTS

| | | | |
|---|---|---|---|
| 5,314,476 A | 5/1994 | Prewett et al. |
| 5,531,791 A | 7/1996 | Wolfinbarger |
| 5,556,379 A | 9/1996 | Wolfinbarger |
| 5,676,146 A | 10/1997 | Scarborough |
| 5,707,962 A | 1/1998 | Chen et al. |
| 5,749,874 A | 5/1998 | Schwartz |
| 5,769,899 A | 6/1998 | Schwartz et al. |
| 5,788,941 A | 8/1998 | Dalmasso et al. |
| 5,797,871 A | 8/1998 | Wolfinbarger |
| 5,820,581 A | 10/1998 | Wolfinbarger |
| 5,895,426 A | 4/1999 | Scarborough et al. |
| 5,948,428 A | 9/1999 | Lee et al. |
| 5,972,368 A | 10/1999 | McKay |
| 5,976,104 A | 11/1999 | Wolfinbarger |
| 5,977,034 A | 11/1999 | Wolfinbarger |
| 5,977,432 A | 11/1999 | Wolfinbarger |
| 6,024,735 A | 2/2000 | Wolfinbarger |
| 6,090,998 A | 7/2000 | Grooms et al. |
| 6,180,606 B1 | 1/2001 | Chen et al. |
| 6,189,537 B1 | 2/2001 | Wolfinbarger |
| 6,200,347 B1 | 3/2001 | Anderson et al. |
| 6,214,369 B1 | 4/2001 | Grande |
| 6,294,041 B1 | 9/2001 | Boyce et al. |
| 6,294,187 B1 | 9/2001 | Boyce et al. |
| 6,305,379 B1 | 10/2001 | Wolfinbarger |
| 6,315,795 B1 | 11/2001 | Scarborough et al. |
| 6,340,477 B1 | 1/2002 | Anderson |
| 6,371,988 B1 | 4/2002 | Pafford et al. |
| 6,436,138 B1 | 8/2002 | Dowd |
| 6,464,983 B1 | 10/2002 | Grotendorst |
| 6,478,825 B1 | 11/2002 | Winterbottom et al. |
| 6,482,231 B1 | 11/2002 | Abatangelo |
| 6,482,233 B1 | 11/2002 | Aebi et al. |
| 6,511,509 B1 | 1/2003 | Ford et al. |
| 6,534,095 B1 | 3/2003 | Moore-Smith et al. |
| 6,576,015 B2 | 6/2003 | Geistlich et al. |
| 6,616,698 B2 | 9/2003 | Scarborough |
| 6,652,593 B2 | 11/2003 | Boyer, II et al. |
| 6,685,626 B2 | 2/2004 | Wironen |
| 6,696,073 B2 | 2/2004 | Boyce et al. |
| 6,716,245 B2 | 4/2004 | Pasquet et al. |
| 6,746,484 B1 | 6/2004 | Liu et al. |
| 6,800,480 B1 | 10/2004 | Bodnar et al. |
| 6,805,713 B1 | 10/2004 | Carter et al. |
| 6,808,585 B2 | 10/2004 | Boyce et al. |
| 6,837,907 B2 | 1/2005 | Wolfinbarger |
| 6,855,169 B2 | 2/2005 | Boyer et al. |
| 6,863,694 B1 | 3/2005 | Boyce et al. |
| 6,902,578 B1 | 6/2005 | Anderson et al. |
| 6,911,045 B2 | 6/2005 | Shimp |
| 6,911,212 B2 | 6/2005 | Gertzman et al. |
| 7,018,412 B2 | 3/2006 | Ferreira et al. |
| 7,048,765 B1 | 5/2006 | Grooms et al. |
| 7,115,146 B2 | 10/2006 | Boyer, II et al. |
| 7,132,110 B2 | 11/2006 | Kay et al. |
| 7,163,691 B2 | 1/2007 | Knaack et al. |
| 7,172,629 B2 | 2/2007 | McKay |
| 7,241,874 B2 | 7/2007 | Thorne |
| 7,297,540 B2 | 11/2007 | Mitrani |
| 7,316,822 B2 | 1/2008 | Binette et al. |
| 7,323,011 B2 | 1/2008 | Shepard et al. |
| 7,335,381 B2 | 2/2008 | Malinin |
| 7,371,409 B2 | 5/2008 | Petersen et al. |
| 7,498,040 B2 | 3/2009 | Masinaei et al. |
| 7,582,309 B2 | 9/2009 | Rosenberg et al. |
| 7,608,113 B2 | 10/2009 | Boyer et al. |
| 7,622,562 B2 | 11/2009 | Thorne et al. |
| 7,662,185 B2 | 2/2010 | Alfaro et al. |
| 7,753,963 B2 | 7/2010 | Boyer et al. |
| 7,785,634 B2 | 8/2010 | Borden |
| 7,807,458 B2 | 10/2010 | Schiller |
| 7,811,608 B2 | 10/2010 | Kay et al. |
| 7,815,926 B2 | 10/2010 | Syring et al. |
| 7,837,740 B2 | 11/2010 | Semler et al. |
| 7,875,296 B2 | 1/2011 | Binette et al. |
| 7,879,103 B2 | 2/2011 | Gertzman et al. |
| 7,883,511 B2 | 2/2011 | Fernyhough |
| 7,931,692 B2 | 4/2011 | Sybert et al. |
| 8,002,813 B2 | 8/2011 | Scarborough et al. |
| 8,002,837 B2 | 8/2011 | Stream et al. |
| 8,021,692 B2 | 9/2011 | Hiles |
| 8,025,896 B2 | 9/2011 | Malaviya et al. |
| 8,039,016 B2 | 10/2011 | Drapeau et al. |
| 8,133,421 B2 | 3/2012 | Boyce et al. |
| 8,137,702 B2 | 3/2012 | Binette et al. |
| 8,163,549 B2 | 4/2012 | Yao et al. |
| 8,167,943 B2 | 5/2012 | Carter et al. |
| 8,197,474 B2 | 6/2012 | Scarborough et al. |
| 8,202,539 B2 | 6/2012 | Behnam et al. |
| 8,268,008 B2 | 9/2012 | Betz et al. |
| 8,292,968 B2 | 10/2012 | Truncale et al. |
| 8,328,876 B2 | 12/2012 | Behnam et al. |
| 8,343,229 B2 | 1/2013 | Coale |
| 8,389,017 B1 | 3/2013 | Starling et al. |
| 8,399,010 B2 | 3/2013 | McKay |
| 8,403,991 B2 | 3/2013 | Ullrich, Jr. et al. |
| 8,409,623 B2 | 4/2013 | Shim et al. |
| 8,435,566 B2 | 5/2013 | Behnam et al. |
| 8,496,970 B2 | 7/2013 | Binette et al. |
| 8,506,632 B2 | 8/2013 | Ganem et al. |
| 8,551,176 B2 | 10/2013 | Ullrich, Jr. et al. |
| 8,563,040 B2 | 10/2013 | Marchosky |
| 8,574,825 B2 | 11/2013 | Shelby et al. |
| 8,585,766 B2 | 11/2013 | Ullrich, Jr. et al. |
| 8,722,075 B2 | 5/2014 | Shimp et al. |
| 8,771,368 B2 | 7/2014 | McKay |
| 8,834,928 B1 | 9/2014 | Truncale et al. |
| 8,859,007 B2 | 10/2014 | Carter et al. |
| 8,883,210 B1 | 11/2014 | Truncale et al. |
| 8,992,964 B2 | 3/2015 | Shelby et al. |
| 9,029,077 B2 | 5/2015 | Song et al. |
| 9,162,012 B2 | 10/2015 | Benham et al. |
| 9,168,140 B2 | 10/2015 | Shi et al. |
| 9,192,695 B2 | 11/2015 | Shi |
| 9,352,003 B1 | 5/2016 | Semler et al. |
| 9,603,710 B2 | 3/2017 | Shi et al. |
| 9,808,558 B2 | 11/2017 | Shi |
| 9,814,803 B2 | 11/2017 | Shi |
| 10,130,736 B1 | 11/2018 | Semler et al. |
| 2007/0185231 A1 | 8/2007 | Liu et al. |
| 2008/0058953 A1 | 3/2008 | Scarborough |
| 2008/0249632 A1 | 10/2008 | Stone et al. |
| 2008/0249638 A1 | 10/2008 | Asgari |
| 2008/0305145 A1 | 12/2008 | Shelby et al. |
| 2010/0168869 A1 | 7/2010 | Long et al. |
| 2010/0196333 A1 | 8/2010 | Gaskins et al. |
| 2010/0241228 A1 | 9/2010 | Syring et al. |
| 2011/0070271 A1 | 3/2011 | Truncale et al. |
| 2012/0213859 A1 | 8/2012 | Shelby et al. |
| 2012/0251609 A1 | 10/2012 | Huang et al. |
| 2013/0189338 A1 | 7/2013 | Drapeau et al. |
| 2014/0093543 A1 | 4/2014 | Morreale |
| 2014/0121772 A1 | 5/2014 | Emerton et al. |
| 2014/0170232 A1 | 6/2014 | Shelby et al. |

(56) References Cited

U.S. PATENT DOCUMENTS

| | | | |
|---|---|---|---|
| 2014/0205674 A1 | 7/2014 | Wei | |
| 2014/0208980 A1 | 7/2014 | Song et al. | |
| 2014/0212471 A1 | 7/2014 | Drapeau et al. | |
| 2014/0212499 A1 | 7/2014 | Cooper et al. | |
| 2014/0220142 A1 | 8/2014 | Song et al. | |
| 2014/0255489 A1* | 9/2014 | Shi | A61L 27/3608 424/549 |
| 2014/0255506 A1 | 9/2014 | Behnam et al. | |
| 2014/0315307 A1 | 10/2014 | March et al. | |
| 2014/0342013 A1 | 11/2014 | He et al. | |
| 2015/0004247 A1 | 1/2015 | Carter et al. | |
| 2015/0011947 A1* | 1/2015 | Anderson | A61K 36/00 604/218 |
| 2015/0012107 A1 | 1/2015 | Koford et al. | |
| 2015/0093429 A1 | 4/2015 | Carter et al. | |
| 2015/0174295 A1 | 6/2015 | Woodell-May et al. | |
| 2015/0182667 A1 | 7/2015 | Guelcher et al. | |
| 2015/0202345 A1 | 7/2015 | Shelby et al. | |
| 2015/0202346 A1 | 7/2015 | Shelby et al. | |
| 2015/0251361 A1 | 9/2015 | Meyer et al. | |
| 2015/0258244 A1 | 9/2015 | Shelby et al. | |
| 2015/0306278 A1 | 10/2015 | McKay | |
| 2016/0129152 A1 | 5/2016 | Shi | |
| 2016/0367728 A1* | 12/2016 | Reves | C08L 89/06 |
| 2017/0072101 A1 | 3/2017 | Bhat et al. | |
| 2017/0203006 A1 | 7/2017 | Carter et al. | |
| 2019/0134265 A1 | 5/2019 | Semler et al. | |

FOREIGN PATENT DOCUMENTS

| | | |
|---|---|---|
| WO | 2013047936 | 4/2013 |
| WO | 2014110284 A1 | 7/2014 |

OTHER PUBLICATIONS

International Search Report and Written Opinion for PCT/US2018/040332, dated Oct. 18, 2018, 11 pages.

Finkemeier, "Bone Grafting and Bone-Graft Substitutes"; The Journal of Cone and Joint Surgery, pp. 454-464; vol. 84-A, No. 3, Mar. 2002.

Gepstein, et al. "Bridging Large Defects in Bone by Demineralized Bone Matrix in the Form of a Powder"; The Journal of Bone and Joint Surgery, pp. 984-992; vol. 69-A, No. 7, Sep. 1987.

Glowacki, et al., Mechanisms of Osteoinduction/Chondroinduction by Demineralized Bone, The Journal of craniofacial surgery, vol. 20(1), pp. 634-638, Feb. 2009.

Honsawek, S., et al., Effects of Demineralized Bone Matrix on Proliferation and Osteogenic Differentiation of Mesenchymal Stem Cells from Human Umbilical Cord, J Med Assoc Thai, vol. 89, Suppl 3, pp. 189-195, (2006).

Mauney, et al., "In Vitro and in Vivo Evaluation of Differentially Demineralized Cancellous Bone Scaffolds Combined with Human Bone Marrow Stromal Cells for Tissue Engineering", Biomaterials, vol. 26, pp. 3173-3185, (2005).

Pietrzak , et al., "Assay of Bone Morphogenetic Protein-2, -4, and -7 in Human Demineralized Bone Matrix", J. Craniofac. Surg., vol. 17, No. 1, pp. 84-90, Jan. 2006.

Reddi, "Role of Morphogenetic Proteins in Skeletal Tissue Engineering and Regeneration", Nat Biotechnol., vol. 16, No. 3, pp. 247-252, (1998).

Schwartz, et al. "Osteoinductivity of Demineralized Bone Matrix is Independent of Donor Bisphosphonate Use"; The Journal of Bone and Joint Surgery; vol. 93-A, No. 24, pp. 2278-2286 Dec. 21, 2011.

Urist, M., "Bone Formation by Autoinduction", *Science*, vol. 150, No. 3698, pp. 893-899. Nov. 12, 1965.

\* cited by examiner

CELLULAR BONE GRAFTS, AND METHODS OF MANUFACTURE AND USE

CROSS-REFERENCES TO RELATED APPLICATIONS

The present patent application claims benefit of priority to U.S. Provisional Patent Application No. 62/527,628 filed Jun. 30, 2017, the contents of which are incorporated by reference in its entirety.

BACKGROUND

The disclosure is generally directed to the field of medical grafts, and in particular, to bone graft compositions, and methods of their use and manufacture. Bone is composed of organic and inorganic material. By weight, bone is approximately 20% water. The weight of dry bone is comprised of inorganic minerals such as calcium phosphate (e.g., 65-70% by weight) and an organic matrix of fibrous protein, predominantly collagen (e.g., 30-35% by weight). Both mineralized and demineralized bone can be used for medical grafting purposes.

A bone graft recruits a host's cells to the site of the bone graft and facilitates new bone growth through osteogenic progenitor cells that can differentiate into osteoblasts. Ideally, a bone graft possesses osteoconductive, osteoinductive, and osteogenic properties to facilitate repair of bone defects, bone fractures and other surgical procedures (e.g., spinal fusions).

Medical grafting procedures often involves the implantation of autogenous, allograft, or synthetic grafts into a patient to treat a particular condition or disease. The use of musculoskeletal allograft tissue in reconstructive orthopedic procedures and other medical procedures has markedly increased in recent years, and millions of musculoskeletal allografts have been safely transplanted. A common allograft is bone. Typically, bone grafts are reabsorbed and replaced over time with the patient's natural bone upon healing. Bone grafts can be used in a variety of indications, including neurosurgical and orthopedic spine procedures for example. In some instances, bone grafts can be used to fuse joints or to repair broken bones or bone defects.

Allograft and autogenous bone are both derived from humans; the difference is that allograft bone is recovered from an individual (e.g., donor) other than the individual (e.g., patient) receiving the graft. Allograft bone is often taken from individuals who have directed that their tissue be donated for medical treatment purposes, upon their death, so that it can be used for living people who are in need of it, for example, patients whose bones have degenerated from cancer. Such tissues represent a gift from the donor or the donor family to enhance the quality of life for other people. Allograft bone graft material is therefore an alternative to autogenous bone material. However, allograft bone graft material is usually rigorously processed and sterilized to reduce the risk of disease transmission or immunological response when implanted in a host who is distinct from the donor (e.g., Graft Versus Host Disease (GVHD)). Typically, allograft bone material processing removes osteogenic and osteoinductive properties from the bone graft material leaving only an osteoconductive scaffold remaining. Thus, delivery of recombinant Bone Morphogenic Proteins (e.g., BMP-2) have been used to stimulate osteogenic and/or osteoinductive mechanisms in patients who have been implanted with an osteoconductive bone graft.

Bone graft compositions and methods currently provide real benefits to patients in need thereof. However, additional improvements are needed to provide improved bone graft compositions, and methods for treating patients. The bone graft compositions, methods of treatment, and manufacture described herein provide further solutions and meet outstanding needs.

BRIEF SUMMARY

In one aspect, provided are methods of manufacturing a bone graft material. Exemplary methods can include combining a radiopaque component with a cancellous bone component to produce the bone graft material. In some instances, the bone graft material comprises native or endogenous living cells. In some instances, the native or endogenous living cells are osteoreparative cells selected from osteoblasts, osteoclasts, fibroblasts, osteocytes and Mesenchymal Stem Cells (MSCs). In some instances, the radiopaque component is non-demineralized cortical bone. In some instances, the radiopaque component comprises non-demineralized cortical bone, barium sulfate, bismuth trioxide, bismuth subcarbonate, tungsten, titanium, zirconium oxide, iodinated polyesters, or iodinated aliphatic monomers. In one embodiment, the radiopaque component is barium sulfate. In some instances, the bone graft material includes a binder comprising one or more of alginic acid, carboxy-methyl cellulose, hyaluronic acid, gelatin, polaxamer, polyvinyl alchol (PVA), polyvinylpyrrolidone (PVP), polylactic acid (PLA), polyglycolide (PG), chitosan, chitin, or a metal salt of any thereof. The metal salt may be an alkali metal salt or alkaline earth metal salt. In some instances, the bone graft material includes an additive comprising a bone morphogenic protein (BMP), fibroblast growth factor-2 (FGF-2), insulin-like growth factor I (IGF-I), insulin-like growth factor II (IGF-II), platelet derived growth factor (PDGF), transforming growth factor beta I (TGFβ-I) or vascular endothelial growth factor (VEGF). In one embodiment, the additive is a recombinant additive (e.g., human recombinant BMP-2 (hrBMP-2). In some instances, the bone graft material comprises periosteum, fascia, or both. In some instances, the bone graft material may comprise demineralized cortical bone. In some instances, the bone graft material is cryopreserved in a cryopreservative. In some embodiments, the cryopreservative comprises dimethyl sulfoxide (DMSO), CS10®, trehalose, dextrose, alpha-tocopherol, stabilized ascorbic acid, resveratrol, methanol, butanediol, propanediol, hydroxyethyl starch, a glycol, or a combination thereof.

According to some embodiments, manufacturing methods may include non-enzymatically processing the cancellous bone to produce a non-enzymatically processed cancellous bone component. In some instances, the non-enzymatic processing includes a passive soaking cycle, whereby the cancellous bone is passively soaked in cell culture media. In some instances, the media includes a mammalian media selected from Minimum Essential Media (MEM), Minimum Essential Medium Eagle (MEME), or Dulbecco's Modified Eagle's Medium/Ham's Nutrient Mixture F-12. In some embodiments, the cell culture media comprises a supplement and/or an antibiotic. In some embodiments, the supplement is Fetal Bovine Serum (FBS), Human Serum, Human Serum Albumin, Bovine Serum Albumin, or Human Platelet Lysate (hPL). In some embodiments, the supplement is an essential or non-essential amino acid supplement (e.g., MEME Amino Acids). In some embodiments, the antibiotic comprises vancomycin, gentamycin, polymyxin B, ciprofloxacin, amphotericin B, or bacitracin.

According to some embodiments, manufacturing methods may include the step of pre-hydrating the binder prior to combining the binder with the cancellous bone and radiopaque components. In some instances, the pre-hydrating step includes soaking the binder in a cell culture media for a period of time, until a gel, gum or putty-like material is formed.

In another aspect, provided is a bone graft material suitable for implantation into a subject. Exemplary bone graft materials include a radiopaque component and a cancellous bone component. In some instances, the cancellous bone component is a non-enzymatically processed cancellous bone component. In some instances, the bone graft material comprises non-demineralized cortical bone. In some instances, the bone graft material includes a binder and/or an additive. In some instances, the bone graft material includes endogenous cells present in native cancellous bone. In some instances, the endogenous cells comprise osteoreparative cells selected from osteoblasts, osteoclasts, osteocytes, fibroblasts, MSCs, or a combination thereof. In some instances, the bone graft material is free, or substantially free (e.g., >90%), of white blood cells (leukocytes) or red blood cells (erythrocytes). In some instances, the bone graft material is free of erythrocytes.

In some instances, the bone graft material contains less than 5% CD4+ cells. In some instances, the bone graft material includes less than 5% CD3+ cells. In some instances, the bone graft material includes less than 5% CD45+ cells. In some instances, the bone graft material includes greater than 50% CD44+ cells. In some instances, the bone graft material includes greater than 30% CD90+ cells. In some instances, the bone graft material includes greater than 10% CD44+ cells which are intact (e.g., viable, living cells) and adhered to the bone graft material. In some instances, the bone graft material comprises periosteum, fascia, or both. In some instances, the bone graft composition comprises between 1,000 and 100 million viable cells per gram of bone graft material. In some instances, the bone graft compositions includes between 10,000 and 60 million viable cells per gram of bone graft material. In some instances, the bone graft composition comprises between 100,000 and 20 million viable cells per gram of bone graft material. In some instances, the bone graft material includes an average cell count of between 1,000 to 50 million MSCs per gram of bone graft material. In some instances, the bone graft material includes an average cell count of between 10,000 to 30 million MSCs per gram of bone graft material. In some instances, the bone graft material includes an average cell count of between 100,000 to 20 million MSCs per gram of bone graft material. In some instances, the bone graft material includes an average cell count of 1 million MSCs per gram of bone graft material. In some instances, the bone graft material includes an average cell count of 5 million MSCs per gram of bone graft material. In some instances, the bone graft includes between 1% and 80% MSCs based on total cell composition of the bone graft material. In some instances, the bone graft includes 5% to 30% MSCs based on total cell composition of the bone graft material. In some instances, the bone graft includes 10% to 50% MSCs based on total cell composition of the bone graft material.

In yet another aspect, provided is a method of treating a subject with a bone graft material. Exemplary treatment methods include administering the bone graft material to the subject (e.g., to a damaged or defective bone of the subject).

In some instances, the bone graft material is applied to a surgical instrument or surgical construct before or during the implantation process (e.g., a spinal cage). In some instances, the bone graft material is administered to a subject to repair a bone fracture. In some instances, the bone graft material is administered to a subject during an orthopedic or neurosurgical procedure. In one embodiment, the surgical procedure is a spinal fusion.

BRIEF DESCRIPTION OF THE DRAWINGS

These figures are intended to be illustrative, not limiting. Although the aspects of the disclosure are generally described in the context of these figures, it should be understood that it is not intended to limit the scope of the disclosure to these particular aspects.

DETAILED DESCRIPTION

I. Introduction

Figure 1:
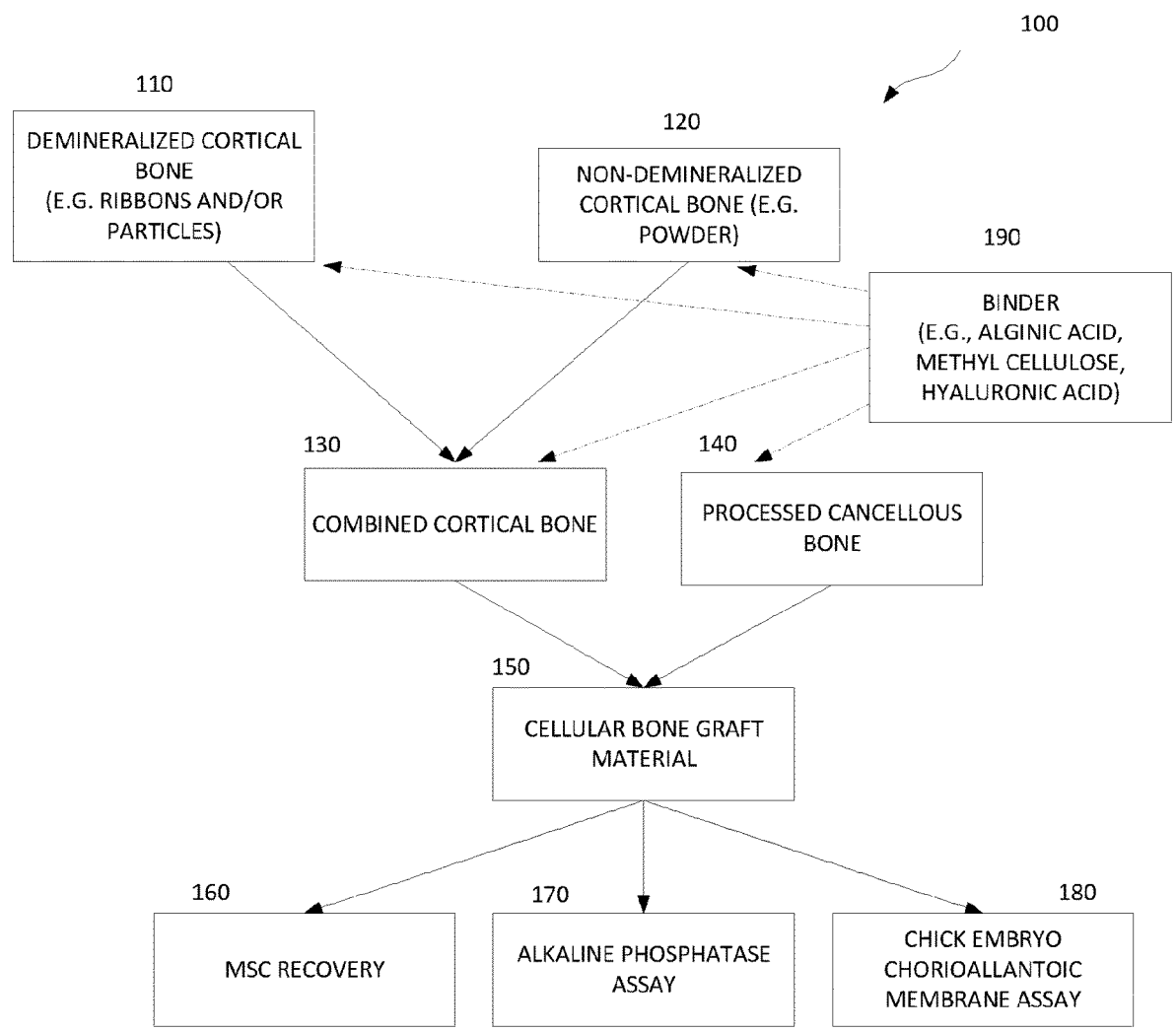
FIG. 1 depicts aspects of a process for manufacturing bone graft material according to an exemplary embodiment of the disclosure.

This disclosure provides compositions, methods, and systems in the field of medical grafts and, particularly, to implantable bone graft material and methods for their manufacture and use. The bone graft material, along with the systems and methods for making and using such bone grafts, as disclosed herein are useful in various industries including orthopedics, reconstructive surgery, dental surgery, and neurosurgery. In exemplary embodiments, the bone graft material can be implanted in a recipient (e.g., patient or subject) for purposes of treating a bone condition in the recipient. In some embodiments, the bone graft material is well suited for promoting osteogenesis (bone growth) and/or bone repair because the bone graft material includes naturally occurring (i.e., native or endogenous) osteoreparative cells. In some embodiments, the osteoreparative cells are adhered to a component of the bone graft material (e.g., cancellous bone). As such, the bone graft material containing osteoreparative cells can be surgically implanted in a recipient resulting in promotion of osteogenesis. In some embodiments, the bone graft material can be prepared such that immunogenic components, such as red (erythrocytes) and/or white (leukocytes) blood cells are removed from the bone graft material.

II. Terms

As used herein "long bones", refers to human skeletal bones that are longer in length than their width (e.g., femur, tibia, fibula, humerus, radius, ulna, metacarpals metatarsals, phalanges and clavicles). The long bones comprise a proximal and distal epiphysis and a long diaphysis (shaft). The diaphysis is separated from the distal and promximal epiphysis by a respective metaphysis section.

As used herein "cortical bone", "cortical bone component", or "compact bone" refers to the hard outer layer of human long bones that are denser than cancellous bone. Cortical bone forms the hard exterior of human bones, typically having a smooth, white, solid surface. Cortical bone accounts for 80% of the total bone mass of an adult human skeleton. Cortical bone comprises multiple microscopic columns called osteon's. Each column has multiple layers of osteoblasts and osteocytes around a central canal called the Haversian canal. Volkmann's canals at right angles connect the osteons together. The cortical bone is covered in a fibrous protein outer layer known as "periosteum" which is composed of bone progenitor cells, such as MSCs and naturally occurring bone stimulating proteins, such as Bone Morphogenic Proteins (BMPs). In some instances, the periosteum is removed from cortical bone before the cortical bone is combined with a radiopaque component, thereby forming the bone graft material.

As used herein "non-demineralized cortical bone component" is a subset of cortical bone wherein the mineral content is retained. Non-demineralized cortical bone is a radiopaque material (see, FIG. 4).

As used herein, "cancellous bone", "cancellous bone component", or "trabecular" is the internal portion of human skeletal bones and comprises a porous network of bone tissue. Cancellous bone has a higher surface-area-to-volume ratio than cortical bone and is therefore less dense making cancellous bone softer and weaker than cortical bone, but more flexible. Cancellous bone is typically found at the proximal ends of long bones (e.g., femur) and within the interior of vertebrae. Cancellous bone is highly vascular and frequently contains red bone marrow where the production of blood cells occurs. Cancellous bone accounts for 20% of the total bone mass of an adult human skeleton and has nearly a ten-fold increase in surface area as compared to cortical bone.

As used herein, "Demineralized Bone Matrix" or "DBM", refers to bone tissue in which the inorganic material (e.g., minerals, such as calcium) have been removed, leaving behind an organic proteinaceous (e.g., collagen) matrix. In some embodiments, a DBM preparation or formulation comprises less than 5% calcium of the original starting amount of calcium (e.g., 1%, 2%, 3%, or 4% calcium). In some embodiments, a DBM preparation or formulation described herein comprises less than 1% calcium by weight. Removal of the inorganic material exposes biologically active BMPs. Thus, DBM is typically considered more biologically active than non-demineralized bone matrix. DBM was observed to produce superior bone grafting properties to non-demineralized allograft bone graft material because removal of the mineral content was found to increase osteoinductivity of the bone graft material (Glowacki, et al., *J Craniofacial Surg*, 2009. 20(1):634-8). Thus, DBM is considered an osteoinductive material.

Processes for demineralizing bone are well known in the art. For example, see, Lewandrowski et al., *J. Biomed Materials Res.*, (1996) 31:365-372; Lewandrowski et al., *Calcified Tissue Int.*, (1997) 61:294-297; and Lewandrowski et al., *J. Ortho. Res.*, (1997) 15:748-756. Generally, the process of preparing DBM includes removing the bone (e.g., aseptically) and treating with an agent (e.g., antibiotic and/or antiviral) to kill infectious agents. The bone is then milled or ground to an appropriate size or shape (e.g., blocks, particles or ribbons), and the mineral content extracted. In one example, bone is soaked in an acid solution to remove the mineral content. After the mineral content is removed, the remaining DBM is malleable and can be further processed and/or formed and shaped for implantation into the recipient. Following implantation, the DBM induces cellular recruitment of the host's cells to the site of implantation and the host cells may eventually differentiate into bone forming cells (e.g., osteoblasts).

As used herein, "Demineralized Cortical Bone" or "DCB" is a subset of DBM and refers to cortical bone in which the inorganic material (e.g., calcium) has been removed. Accordingly, DCB possesses osteoinductive properties (see, Honsawek et al., 2000).

As used herein, "osteoinductive" refers to the ability of an implant material or compound to recruit host cells to the site of implantation to form new bone. Osteoinductivity score refers to a score ranging from 0 to 4 as determined by Edwards et al, *Clin. Ortho. & Rel. Res.*, (1998) 357:219-228, or other equivalent method. In the Edwards method, a score of "0" represents no new bone growth, a score of "1" represents between 1% and 25% of the implant involved in new bone growth, a score of "2" represents between 26% and 50% of the implant involved in new bone growth, a score of "3" represents between 51% and 75% of the implant involved in new bone growth, and a score of "4" represents >75% of the implant involved in new bone growth. Typically, the score is assessed 28 days after implantation, although it may be assessed earlier (e.g., 7, 14, or 21 days). In some instances, the score may be assessed as late as 100 days (e.g., 40 or 60 days) after implantation. Osteoinductivity may be assessed in humans but is generally performed on athymic rats (supra).

As used herein, "osteoconductive" refers to the ability of an implant material (e.g., bone graft material) to serve as a template or scaffold on which new bone growth may occur.

As used herein, "osteogenic" refers to an implant material containing living cells capable of differentiation into new bone tissue. An osteogenic implant may contain osteochondroprogenitor cells, such as MSCs that can differentiate into bone forming cells (e.g., osteoblasts). In some instances, the osteogenic implant material comprises endogenous living cells from the donor of the implant material. In some embodiments, the living cells include MSCs, osteoblasts, osteoclasts, osteocytes, or a combination thereof.

As used herein, an "osteoreparative cell" refers to a viable, living cell population present in the bone graft material capable of differentiating into new bone tissue. An osteoreparative cell can include an MSC, osteoblast, osteoclast, osteocyte, fibroblast, or a combination thereof. In some instances, osteoreparative cells can be adhered or attached to a component of the bone graft material (e.g., cancellous bone). In other embodiments, osteoreparative cells can be added to the bone graft material prior to implantation in a subject (e.g., before cryopreservation of the bone graft material or after thawing of the cryopreserved bone graft material).

As used herein, a "native" or "endogenous cell" refers to a living cell present in a bone graft material or a component thereof (e.g., cancellous bone or cortical bone) that is capable of performing cellular functions, such as transportation of molecules, metabolism, and reproduction. A native or endogenous cell is a viable cell and can therefore be detected, for example, by an assay that measures secretion or production of a compound by the native or endogenous cell (e.g., alkaline phosphatase assay).

As used herein, "Bone morphogenetic protein" or "BMP" refer to a group of growth factors that stimulate bone growth (i.e., osteogenic) and can differentiate MSCs into osteochondoprogenitor cells that form osteoblasts (i.e., osteoinductive). These proteins exist naturally in cortical bone and can be recombinantly applied to bone graft materials (e.g., added to bone graft material). Of notable interest are BMP2, BMP3, BMP4, BMP6, and BMP7.

Bone morphogenetic protein 2 (BMP2) is a protein that in humans is encoded by the BMP2 gene (see, GenBank Gene ID: 650). BMP2 potently induces osteoblast differentiation in a variety of cell types (Marie et al., *Histol. Histopathol.*, 2002, 17(3):877-85) and stimulates production of new bone growth (see, Urist, *Science*, 1965, 150 (3698): 893-9). Recombinant forms of BMP2 have been observed to stimulate bone growth (see, Geiger et al., *Adv. Drug Deliv. Rev.* 2003, 55(12):1613-29). Clinical studies of BMP2 were shown to successfully stimulate spinal fusion equal to, or better than, a patient's own bone graft material. BMP2 has received FDA approval for use in anterior lumbar interbody fusion in spine cages.

Bone morphogenetic protein 7 (BMP7) also known as osteogenic protein-1 (OP1) is a protein that in humans is encoded by the BMP7 gene (see, GenBank Gene ID: 655 and Hahn et al., *Genomics*, (1992), 14(3):759-62). Like other members of the BMP family of proteins, BMP7 plays a role in the transformation of mesenchymal cells into bone and cartilage.

As used herein, "additive" refers to a compound or material present in the bone graft material that promotes new bone growth. As set forth herein, exemplary additives include BMPs (e.g., BMP2 and BMP7), fibroblast growth factor-2 (FGF-2), insulin-like growth factors I or II (IGF-I or IGF-II), platelet derived growth factor (PDGF), transforming growth factor-β or vascular endothelial growth factor (VEGF). In some instances, the additive is added to the bone graft material or a component thereof (e.g., cancellous bone). In some embodiments, the additive is endogenous to the bone graft material (e.g., BMP-2), or a component thereof (e.g., present in non-demineralized cortical bone). In some instances, two (or more) additives are present in the bone graft material, where a first additive is endogenous to the bone graft material and a second additive is added to the bone graft material (e.g., mixed with the bone graft material prior to implantation into a subject).

As used herein, "radiopaque" or "radiopaque component" refers to a compound or material that obstructs the passage of radiant energy through matter, such as bone. The compounds or materials are often dense metal powders (e.g., tungsten or barium) that affect energy attenuation of photons in an X-ray beam as it passes through matter, reducing the intensity of the photons by absorbing or deflecting them. Because these compounds and materials exhibit a higher attenuation coefficient than soft tissue or bone, they appear lighter or opaque on a fluoroscope or X-ray film. This visibility can provide contrast to accurately position the bone graft material (e.g., when molded or inserted into surgical instruments, such as spinal cages) or confirm positioning of the bone raft material in the intended area of the recipient.

As used herein, "periosteum" refers to a connective tissue membrane that covers the outer surface of human long bones. In some instances, bone graft materials described herein comprises periosteum, for example in the form of periosteum fibers, prepared by milling or grinding of cortical bone that has not had the periosteum layer removed. In some instances, the cortical bone component comprises cortical bone and periosteum fibers, where the periosteum fibers are either endogenous to the cortical bone component or have been supplemented from the same source (e.g., same donor) or another source (e.g., different donor) and added to the cortical bone.

As used herein, "fascia" refers to a connective fibrous tissue usually found in the lower limbs (e.g., Fascia lata). In some instances, bone graft materials described herein comprises fascia, for example in the form of fascia fibers. In some instances, the cortical bone component comprises cortical bone and fascia fibers, where the fascia fibers are either endogenous to the cortical bone component (e.g., from the same donor) or have been supplemented from another source (e.g., different donor) and added to the cortical bone.

As used herein, "non-enzymatically" refers to a method of processing cancellous bone for use in bone graft material that does not include an enzymatic processing step. In some embodiments, non-enzymatically processing of cancellous bone refers to incubating the cancellous bone in a cell culture medium, such as DMEM and FBS, for a period of time (e.g., 30 minutes or 1 hour) and optionally, decanting the cell culture media after the period of time (e.g., a passive soaking cycle). In one embodiment, the passive soaking cycle may be repeated more than once (e.g., 1 to 5 times) to process the cancellous bone non-enzymatically. The passive soaking cycle may optionally include gentle rotation or swirling to agitate or move the cancellous bone but not to the extent that it disrupts the integrity of the endogenous cellular components of the cancellous bone. Alternatively, cancellous bone can be processed for use in bone graft material using a chemical solution, e.g., an acid solution, for a period of time (e.g., 1 hour) and optionally, decanting the acid solution after incubation for one hour.

As used herein, "binder" refers to a compound or material that is added to the bone graft material or a component thereof that improves the handling, cohesiveness, and malleable properties of the bone graft material, as compared to absence of the binder in the bone graft material. In some instances, a binder can be used to produce bone graft materials having a gel, gum, or putty-like consistency. In some instances, a binder improves the handling of the bone graft material by allowing the bone graft material to be readily manipulated without further processing, and that once molded into a desired conformation, retains its shape and size. In some instances, bone graft materials as described herein retain their size and shape after implantation (e.g., in a spinal cage) during irrigation of the surgical site after implantation. As set forth herein, exemplary binders include alginic acid, carboxymethyl cellulose, hyaluronic acid, gelatin, polaxamer, polyvinyl alcohol (PVA), polyvinylpyrrolidone (PVP), polylactic acid (PLA), polyglycolide (PG), chitosan, chitin, and alkali metal salts or alkaline earth metal salts of any thereof. Suitable alkali metal salts include sodium and potassium. Suitable alkaline earth metal salts include calcium. In some instances, a binder is added to the bone graft material. In some instances, two (or more) binders are present in the bone graft material, where a first binder performs a first function (e.g., produces a gel) and the second binder performs a second function (e.g., creates a covalent or hydrogen bond).

As used herein, "cryopreservation" refers to a process by which bone graft material, cancellous bone, cortical bone, or other biological components (e.g., semen), are cooled and frozen in a controlled manner, suitable for long-term storage (e.g., at −80° C.), typically using liquid nitrogen, dry ice (solid carbon dioxide), or refrigeration. Generally, material to be cryopreserved is incubated, soaked, or coated with a "cryoprotectant". However, some traditional cryoprotectants are toxic to cells at high concentrations (e.g., DMSO). Commercial devices or kits for cryopreservation are available including for example, "Mr. Frosty" by ThermoFisher Scientific. Generally, tubes, vials, or jars containing biological material to be cryopreserved are incubated, soaked, or bathed with a cryoprotectant for a defined period of time and placed under suitable cooling conditions (e.g., liquid nitrogen) such that the biological material cools at a rate of approximately −1° C. per minute until frozen (e.g., rate controlled freezing). The biological material may be left longer than the time taken to visually freeze the biological material (e.g., 2 to 4 hours) and can then be transferred to long-term storage (e.g., −80° C. or −196° C.) until desired.

As used herein "cryoprotectant" refers to a class of molecules used to protect biological components (e.g., bone graft materials or bone graft components, such as cortical bone or cancellous bone) from freezing damage due to ice formation. Generally, cryoprotectants penetrate the biological component before the biological component is frozen. Additionally, it is preferable that the cryoprotectant is not toxic at the concentration used to perform the cryopreservation process. Mixtures of cryoprotectants have been found to be less toxic than a single-agent cryoprotectant (Best et al., (2015) *Rejuvenation Res.*, 18(5):422-436). Conventional cryoprotectants include glycols, such as ethylene glycol, propylene glycol, and glycerol, trehalose, sucrose, 2-methyl-2,4-pentanediol (MPD) and dimethyl sulfoxide (DMSO).

As used herein, "treating" and "treatment" when used in connection with a disease or condition refer to executing a protocol that can include a bone repair or replacement procedure, where the bone implant is administered to a subject (e.g., patient), in order to alleviate signs or symptoms of the disease or condition. Alleviation can occur prior to signs or symptoms of the disease or condition appearing, as well as after their appearance. Thus, treating or treatment includes preventing or prevention of disease or undesirable condition. In addition, treating, treatment, preventing or prevention does not require complete alleviation of signs or symptoms, does not require a cure, and specifically includes protocols that have only a marginal effect on the subject. In some instances, treating includes treating a bone fracture. In some embodiments, treating includes repair of a bone defect.

III. Compositions

In one aspect, the disclosure generally relates to bone graft compositions, referred to herein as bone graft material. The bone graft material can be used, for example, in orthopedic and neurosurgical procedures. Additionally, the bone graph material is suitable for surgical procedures because it contains a radiopaque component that allows for detection of the bone graft material in a subject upon imaging (e.g., X-ray imaging). In some instances, the bone graft material includes a binder which provides superior handling and cohesiveness properties as opposed to bone graft compositions lacking the binder.

In some embodiments, the bone graft material comprises a cancellous bone component and a radiopaque component.

According to some embodiments, the cancellous bone component can include cancellous bone obtained from donor-derived vertebral bodies, ileum, or long bones. In some cases, the cancellous bone component can include cancellous bone obtained from donor-derived Gerdy's tubercle on the proximal metaphysis of the tibia. In some embodiments, the cancellous bone can be present in the form of cubes, spheres, irregularly shaped granules, or other particles or particle shapes, as well as solid constructs made of demineralized bone. In some cases, the cancellous bone can be present in the form of ground chips, with a particle size range between 100 μm and 10 mm. In some cases, the cancellous bone can be present in the form of ground chips, with a particle size range between 200 μm and 7 mm, 500 μm and 5 mm, 1 mm and 4 mm, and 300 μm and 2 mm.

In some embodiments, the cancellous bone can be obtained from a deceased donor. In some embodiments, the cancellous bone can be recovered, and modified with a demineralization protocol, a decellularization protocol, or both a demineralization protocol and a decellularization protocol, to obtain processed cancellous bone. Exemplary demineralization protocols are disclosed in U.S. Patent Publication Nos. 2014/0255489; 2017/0035937 and U.S. Pat. No. 9,907,882, the contents of which are incorporated herein by reference. Exemplary decellularization protocols are disclosed in U.S. Patent Publication No. 2014/0255489, the contents of which are incorporated herein by reference. In some embodiments, demineralization can include the use of an acid solution (e.g., hydrochloric acid). In some instances, the concentration of the acid solution is between 0.05 N and 5 N. For example, the acid solution concentration may be between 0.05 N and 5 N, between 2.5 N and 3 N, between 0.05 N and 0.1 N, between 0.05 N and 0.5 N, or between 0.1 N and 0.5 N. Depending on the nature of the bone being processed, or the desired final product, different acid solution concentrations may be chosen. In one example, an acid solution of 2.5 N to 3.5 N may be used to demineralize large pieces of bone, particularly cortical bone. In another example, an acid solution of 0.1 N to 2 N may be used to demineralize cancellous bone. In another example, an acid solution of 0.5 N to 1 N may be used to demineralize cancellous bone. In some instances, the ratio of bone tissue to acid solution is at least 14 g of bone tissue to 100 mL of acid solution. In some instances, the ratio of bone tissue weight to acid solution volume may be less than 1:5. In some instances, the ratio of bone tissue weight to acid solution volume may be 1:10 or greater. In one example, the acid solution (vol) to the bone tissue (g) ratio may be between 50 mL:1 g and 5 mL:1 g. In general, increasing the volume of acid solution in relation to the amount of bone does not negatively impact the demineralization process.

In some embodiments, cancellous bone can be recovered from a donor and modified with a non-enzymatic process (e.g. passive soaking) that removes erythrocytes (red blood cells), leukocytes, and other immunogenic or undesirable components from the cancellous bone, while blood-derived mesenchymal stem cells (MSCs) remain intact and adhered or attached to the cancellous bone. MSCs are a species of osteoreparative cells, and have the capacity to differentiate into bone and other mesenchymal tissues. MSCs can also contribute to the regeneration of bone and other mesenchymal tissues. In some embodiments, the non-enzymatic treatment of cancellous bone does not affect MSCs or optionally, other osteoreparative cells, attached to the cancellous bone, thus those cells retain their natural characteristics for repairing bone damage. In some embodiments, the non-enzymatic treatment of cancellous bone does not alter MSCs by detachment from the cancellous bone. In some embodiments, native MSCs in the cancellous bone are not exposed to growth factors in an in vitro expansion process prior to formation of the bone graft material.

In some cases, a passive soaking protocol can involve placing the cancellous bone in a container of cell culture media, such as MEM and FBS, for a period of time. In some cases, the passive soaking can be from 2-60 minutes. In some cases, the passive soaking can be 5 minutes or 10 minutes. In some cases, the passive soaking can be 20 or 30 minutes. In some cases, the media is a Minimum Essential Medium Eagle but other suitable media are known in the art. In some cases, the media may include a supplement. In some instances, the supplement may be a serum such as FBS. The supplement may be added to the medium at a concentration of 5% to 10%. In some cases, the supplement is Human Platelet Lysate (hPL). In some cases, the media can include an anticoagulant, such as ACD-A Anticoagulant Citrate Dextrose Solution, Heparin, Solution A (Citra Labs, Braintree, Mass.). In some cases, the media can include a material that degrades DNA, such as deoxyribonuclease or DNase. The volume of media used to soak the cancellous bone may depend on the amount of cancellous bone being processed. For example, 100 grams of ground cancellous can be soaked in 200-300 ml of media. In some cases, the passive soaking protocol is performed at room temperature (e.g., 25° C.). In some cases, the passive soaking protocol is performed at a temperature between 4° C. and 37° C. In some cases, the passive soaking protocol is performed at 37° C. The passive soaking protocol can be performed as a "standing still" soak or rinse, where the cancellous bone is place in the media, and then the media is poured off. In some cases, the passive soaking protocol can include any number of desired soaking cycles (e.g. 1-5, or more soaking cycles).

In some cases, the cancellous bone is not treated with active rinsing or shaking, as these steps may remove or compromise blood-derived mesenchymal stem cells (MSCs) adhered or attached to the cancellous bone. In some cases, the cancellous bone is not treated with sonication, as sonication may remove or compromise blood-derived mesenchymal stem cells (MSCs) adhered or attached to the cancellous bone.

In some embodiments, the cancellous bone is not subjected to, or treated with, any growth protocols, culturing protocols, expansion protocols, passaging protocols, or the like. As such, the cancellous bone can be prepared directly from bone from a donor, for example by milling and/or grinding. Any suitable method of milling or grinding cancellous bone may be used to produce the cancellous bone component. Exemplary grinding or milling protocols are disclosed in U.S. Patent Publication No. 2012/0258178, the contents of which are incorporated herein by reference.

In some embodiments, the cancellous bone can be present at 20% to 90% (w/w) of the bone graft material. In some embodiments, the cancellous bone can be present at 30% to 80% (w/w), 40% to 60% (w/w), 20% to 40% (w/w), 20% to 50% (w/w), and 40% to 90% (w/w) of the bone graft material.

In some embodiments, the radiopaque component is non-demineralized cortical bone. In some embodiments, the radiopaque component comprises non-demineralized cortical bone, barium sulfate, bismuth trioxide, bismuth subcarbonate, tungsten, titanium, zirconium oxide, iodinated polyesters, or iodinated aliphatic monomers. In one embodiment, the radiopaque component is barium sulfate.

According to some embodiments, the non-demineralized cortical bone component can be present in powder form. In some instances, the non-demineralized cortical bone component can be present at 10% (w/w) of the cellular bone graft material. In some instances, the non-demineralized cortical bone component can be present at 5% to 30% (w/w) of the cellular bone graft material such as, for example, 5%, 10%, 15%, 20%, 25%, or 30% (w/w). In some cases, the non-demineralized cortical bone component can be present in particulate form, and the particles can have an average diameter within a range from 100 microns to 4 mm. In some embodiments, the non-demineralized cortical bone component functions to provide, among other things, an amount of radiopacity to the bone graft material. In some embodiments, the non-demineralized cortical bone component can be replaced by or supplemented with another radiopaque component. Exemplary radiopaque components include, for example, non-demineralized cortical bone, barium sulfate, bismuth trioxide, bismuth subcarbonate, titanium, zirconium oxide, iodinated polyesters and iodinated aliphatic monomers. Any suitable method of milling or grinding cortical bone may be used to produce the non-demineralized cortical bone component. Exemplary grinding or milling protocols are disclosed in U.S. Patent Publication No. 2012/0258178, the contents of which are incorporated herein by reference.

In some embodiments, the bone graft material can further comprise a demineralized cortical bone component, which can include ribbons or other particles such as those described in U.S. patent application Ser. No. 15/431,309, U.S. Patent Publication No. 2017/0035937, and U.S. Pat. No. 9,486,556, the contents of which are incorporated herein by reference. In some cases, the demineralized cortical bone component can include particles such as those described in U.S. Patent Publication Nos. 2014/0255489 and 2017/0035937, the contents of which are incorporated herein by reference. Any suitable method of demineralization may be used to produce demineralized cortical bone. In some embodiments, the demineralized cortical bone component can be present at 50% (w/w) of the bone graft material. In some embodiments, the demineralized cortical bone component can be present at up to 50% (w/w) of the bone graft material. In some embodiments, the demineralized cortical bone component can be present at, for example, 1% to 40% (w/w), 10-50% (w/w), 1-15% (w/w), 5-20% (w/w), 15-30% (w/w), 10-50% (w/w), or 30-50% (w/w) of the bone graft material.

In some embodiments, the bone graft material can further comprise periosteum and/or fascia. Fascia is a flexible fibrous tissues that contains collagen fibers formed by fibroblasts. The present disclosure encompasses techniques for obtaining fascia fibers, processing of fascia fibers for use in a bone graft material, and administering such compositions to a subject. In some embodiments, fascia may be prepared for inclusion in a bone graft material according to the methods described in US Patent Publication No: 2014/027179. In some embodiments, the amount of fascia present in the bone graft material can be from 0.5% by weight to 10% by weight based on the total weight of the bone graft material. In some embodiments, the amount of fascia present in the bone graft material can be from 1% by weight to 5% by weight based on the total weight of the bone graft material. In some embodiments, the bone graft material can comprise periosteum. Periosteum a type of tissue that is involved early during normal bone fracture repair process and can recruit various cell types (e.g., MSCs) and bone growth factors (e.g., BMPs) to facilitate bone fracture repair. Currently, periosteum is discarded during the manufacture of allograft material. The present disclosure encompasses techniques for obtaining periosteum, processing periosteum for use in a bone graft material, and administering such compositions to a subject. In some embodiments, periosteum may be prepared for inclusion in the bone graft material according to the methods described in U.S. Pat. No. 9,907,882. In some embodiments, the amount of periosteum present in the bone graft material can be from 0.5% by weight to 10% by weight based on the total weight of the bone graft material. In some embodiments, the amount of periosteum present in the bone graft material can be from 1% by weight to 5% by weight based on the total weight of the bone graft material. In some embodiments, periosteum fibers, fascia fibers, or a combination thereof, can be combined with the radiopaque component prior to combining the radiopaque component with the cancellous bone component to form the bone graft material.

In some embodiments, the bone graft material comprises one or more cell populations of native or endogenous cells. In some embodiments, the native or endogenous cells are osteoreparative cells. In some embodiments, osteoreparative cells comprise osteoblasts, osteoclasts, osteocytes, fibroblasts, Mesenchymal Stem Cells (MSCs), or a combination thereof. In some embodiments, osteoreparative cells are adhered to or attached to a component of the bone graft material (e.g., cancellous bone) or the bone graft material. In some embodiments, the bone graft material can be supplemented with osteoreparative cells prior to implantation in a subject.

In some embodiments, the cell populations of native or endogenous cells (e.g., osteoreparative cells, such as MSCs) associated with the bone graft material (or component thereof) are not enriched prior to implantation into a recipient. In some embodiments, the cell populations of native or endogenous cells (e.g., MSCs) associated with the bone graft material (or component thereof) are not purified prior to implantation into a recipient. In some embodiments, the cell populations of native or endogenous cells (e.g., MSCs) associated with the bone graft material (or component thereof) are not cultured prior to implantation into a recipient. In some embodiments, the cell populations of native or endogenous cells (e.g., MSCs) associated with the bone graft material (or component thereof) are not expanded in vitro prior to implantation into a recipient. In some embodiments, the cell populations of native or endogenous cells (e.g., MSCs) associated with the bone graft material (or component thereof) are not isolated prior to implantation into a recipient. In some embodiments, the cell populations of native or endogenous cells (e.g., MSCs) associated with the bone graft material (or component thereof) are not treated with any chemical and/or enzymatic processes (e.g. with one or more protein digestive enzymes) that could loosen or detach the native or endogenous cells from the bone graft material (or component thereof) (e.g., collagenase treatment). In some embodiments, the cell populations of native or endogenous cells (e.g., MSCs) associated with the bone graft material (or component thereof) are not treated with collagenase prior to implantation into a recipient. In some embodiments, the cell populations of native or endogenous cells (e.g., MSCs) associated with the bone graft material corresponds to a native population of MSCs associated with cancellous bone. In some embodiments, the MSCs are adult MSCs. In some cases, the MSCs originate from a donor's bone marrow.

In some embodiments, the bone graft material can be supplemented with osteoreparative cells. Thus, the final product (e.g. packaged graft bone graft material), may include floating (or non-adhered) osteoreparative cells (e.g., MSCs).

In some embodiments, the bone graft material can further comprise an additive. In some embodiments, the additive comprises a bone morphogenic protein (BMP), fibroblast growth factor-2 (FGF-2), insulin-like growth factor I (IGF-I), insulin-like growth factor II (IGF-II), platelet derived growth factor (PDGF), transforming growth factor beta I (TGFβ-I), vascular endothelial growth factor (VEGF) or a combination thereof. In one embodiment, the additive is a recombinant additive (e.g., human recombinant BMP-2 (hrBMP-2). In some instances, the additive is added to the bone graft material or a component thereof (e.g., cancellous bone). In some embodiments, the additive is endogenous to the bone graft material (e.g., BMP-2), or a component thereof (e.g., non-demineralized cortical bone). In some instances, two (or more) additives are present in the bone graft material, where a first additive is endogenous to the bone graft material and a second additive is supplemented to the bone graft material (e.g., mixed with the bone graft material prior to implantation into a subject). It will be appreciated that the amount of additive used will vary depending upon the type of additive, the specific activity of the additive employed, and the intended use of the composition. The desired amount is readily determinable by the practitioner in the art.

In some embodiments, the bone graft material further comprises a binder. In some instances, the binder provides superior handling and cohesiveness properties as opposed to bone graft compositions lacking the binder. In some embodiments, the binder comprises one or more of alginic acid, methyl cellulose (e.g., carboxy or hydroxypropyl methyl cellulose), hyaluronic acid, gelatin, polaxamer, polyvinyl alchol (PVA), polyvinylpyrrolidone (PVP), polylactic acid (PLA), polyglycolide (PG), chitosan, chitin, or a metal salt of any thereof. The metal salt may be an alkali metal salt or alkaline earth metal salt. In some embodiments, the bone graft material or a component thereof is incubated with a binder to form a gum, gel or putty-like consistency.

In some embodiments, the bone graft material is combined with a binder to form a flowable, syringeable, putty-like material. For example, a putty-like material can be delivered through a cannula or other syringe attachment to the defect site (see, for example U.S. patent application Ser. No. 13/712,295, the entire content of which is incorporated herein by reference for all purposes). A putty-like bone graft material can possess improved handling and cohesiveness properties as opposed to bone graft materials of a powder or liquid form. For example, putty-like bone graft compositions can stay in place upon implantation, persist at the site of the application (e.g., bone defect area), and resist removal by irrigation and/or contact with blood.

In some embodiments, the bone graft material is free, or substantially free (i.e., >90%), of white blood cells (leukocytes) or red blood cells (erythrocytes). In some embodiments, the bone graft material is at least 91%, 92%, 93%, 94%, 95%, 96%, 97%, 98%, 99%, or 100% free of erythrocytes. In some embodiments, the bone graft material is at least 91%, 92%, 93%, 94%, 95%, 96%, 97%, 98%, 99%, or 100% free of leukocytes. In some embodiments, the bone graft material is free, or substantially free (i.e., >90%), of B cells or T cells. In some embodiments, the bone graft material is at least 91%, 92%, 93%, 94%, 95%, 96%, 97%, 98%, 99%, or 100% free of B cells. In some embodiments, the bone graft material is at least 91%, 92%, 93%, 94%, 95%, 96%, 97%, 98%, 99%, or 100% free of T cells.

In some embodiments, the bone graft material can comprise less than 5% CD4+ cells based on total cell composition of the bone graft material. In some embodiments, the bone graft material can contain less than 5% CD3+ cells based on total cell composition of the bone graft material. In some embodiments, the bone graft material can include less than 5% CD45+ cells based on total cell composition of the bone graft material.

In some instances, the bone graft material can comprise more than 50% CD44+ cells based on total cell composition of the bone graft material. In some instances, the bone graft material can comprise more than 50% CD90+ cells based on total cell composition of the bone graft material. In some embodiments, the bone graft material can comprise more than 60% CD44+ cells based on total cell composition of the bone graft material, wherein the CD44+ cells are adhered to at least one component of the bone graft material (e.g., cancellous bone).

In some embodiments, less than 5% of the total cell composition of the bone graft material are erythrocytes. In some embodiments, less than 1% of the total cell composition of the bone graft material are erythrocytes. In some embodiments, the bone graft material is free of erythrocytes (i.e., erythrocytes are not detected under test conditions). Erythrocytes may be detected by any suitable method known in the art, including but not limited to, microscopy, hemocytometer, or the use of antibodies to detect red blood cells in the bone graft material.

In some embodiments, less than 5% of the total cell composition of the bone graft material are leukocytes. In some embodiments, less than 1% of the total cell composition of the bone graft material are leukocytes. In some embodiments, the bone graft material is free of leukocytes (i.e., leukocytes are not detected under test conditions). Leukocytes may be detected by any suitable method known in the art, including but not limited to, microscopy, hemocytometer, or the use of antibodies to detect the expression of specific cell surface markers associated with white blood cells (e.g., CD45+).

In some embodiments, less than 10% of the total cell composition of the bone graft material expresses cell surface marker CD45+. In some embodiments, less than 8%, 5%, 4%, 3%, 2%, or 1% of the total cell composition of the bone graft material expresses cell surface marker CD45+. In some embodiments, less than 1% of the total cell composition of the bone graft material expresses cell surface marker CD45+.

In some embodiments, less than 10% of the total cell composition of the bone graft material expresses cell surface marker CD4+. In some embodiments, less than 5%, 4%, 3%, or 2% of the total cell composition of the bone graft material expresses cell surface marker CD4+. In some embodiments, the bone graft material contains less than 1% of the total cell composition expressing cell surface marker CD4+.

In some embodiments, less than 5%, 4%, 3%, or 2% of the total cell composition of the bone graft material expresses cell surface marker CD3+. In some embodiments, the bone graft material contains less than 1% of the total cell composition expressing cell surface marker CD3+.

In some embodiments, the bone graft material comprises greater than 50% of the total cell composition expressing cell surface marker CD44+. In some embodiments, the bone graft material contains greater than 1%, 5%, 10%, 20%, 30%, 40%, 50%, 60%, 70%, 80%, or 90% of the total cell composition expressing cell surface marker CD44+.

In some embodiments, the bone graft material comprises greater than 50% of the total cell composition expressing cell surface marker CD90+. In some embodiments, the bone graft material contains greater than 1%, 5%, 10%, 20%, 30%, 40%, 50%, 60%, 70%, 80%, or 90% of the total cell compositions expressing cell surface marker CD90+.

In some embodiments, the bone graft material can comprise between 1,000 and 100 million native cells per gram of bone graft material. In some embodiments, the bone graft material can comprise between 10,000 million and 60 million native cells per gram of bone graft material. In some embodiments, the bone graft material can comprise between 100,000 and 20 million native cells per gram of bone graft material. In some embodiments, the bone graft material can comprise an average cell count of 1,000 to 50 million MSCs per gram of bone graft material. In some embodiments, the bone graft material can comprise an average of 10,000 to 30 million MSCs per gram of bone graft material. In some embodiments, the bone graft material can comprise an average of 100,000 to 20 million MSCs per gram of bone graft material. In some embodiments, the bone graft material can comprise an average of 250,000 to 10 million MSCs per gram of bone graft material. In some embodiments, the bone graft material can comprise an average of 500,000 to 5 million MSCs per gram of bone graft material. In some embodiments, the bone graft material can comprise between 1% and 80% MSCs based on total cell composition of the bone graft material. In some embodiments, the bone graft material can comprise 5% to 30% MSCs based on total cell composition of the bone graft material. In some instances, the bone graft includes 10% to 50% MSCs based on total cell composition of the bone graft material.

In one embodiment, the bone graft material comprises a radiopaque component in an amount from about 1% to about 20% (w/w), a binder in an amount from about 1% to about 10% (w/w), a cell culture media in an amount from about 1% to about 20% (w/w), and a cancellous bone component in an amount from about 50% to about 97% (w/w), wherein the cancellous bone component comprises less than 5% erythrocytes or leukocytes and contains an average cell count of between 1,000 to 50 million osteoreparative cells per gram of bone graft material. In one embodiment, the osteoreparative cells are MSCs. In some instances, the cancellous bone component comprises ground cancellous bone (cancellous bone powder). In some instances, the radiopaque component is cortical bone. In some instances, the cortical bone is ground cortical bone (cortical bone powder). In some instances, the binder is a hydrated binder. In some instances, the binder is alginic acid (also referred to as alginate). In some instances, the alginic acid is high molecular weight alginic acid. In some instances, the cell culture media is serum free.

In one embodiment, the bone graft material comprises 10% non-mineralized cortical powder (w/w), 4% alginic acid (w/w), 16% DMEM cell culture media (w/w), and 70% cancellous bone (w/w), wherein the cancellous bone contains an average cell count of between 1,000 to 50 million osteoreparative cells per gram of bone graft material. In one embodiment, the osteoreparative cells are MSCs. In some instances, the alginic acid is high molecular weight alginic acid. In some instances, the DMEM is serum free.

In one embodiment, the bone graft material comprises 10% non-mineralized cortical powder (w/w), 4% alginic acid (w/w), 16% DMEM cell culture media (w/w), and 70% cancellous bone (w/w), wherein the cancellous bone has a total cell composition of between 1% and 80% MSCs per gram of bone graft material. In some instances, the alginic acid is high molecular weight alginic acid. In some instances, the DMEM is serum free.

In some embodiments, each component of the bone graft material can be obtained from a single donor. In some embodiments, the cancellous bone and the cortical bone can be obtained from the same donor. In some embodiments, the donor is a deceased human donor (e.g., a cadaver). In some embodiments, the additive can be obtained from a different donor.

Often, when tissue such as cortical or cancellous bone is recovered from a deceased donor for use in manufacturing the cellular bone graft material, the tissue is recovered within 36 hours of asystole, or the ischemic time has been less than 36 hours. In other words, the donor has been deceased for no longer than 36 hours.

A. Donor

The bone graft material can be obtained from one or more donors. In some embodiments, the bone graft material is obtained from a single donor. In some embodiments, the recipient of the bone graft material is the same individual as the donor (autologous). In some embodiments, the recipient of the bone graft material is a different individual to the donor (allogeneic). The donor may be human or non-human animal. Non-human animals include non-human primates, rodents, canines, felines, porcines, bovines, equines, ovines, and the like. In some embodiments, the bone graft material is obtained from a living human donor. In some embodiments, the bone graft material is obtained from a deceased human donor (e.g., a cadaver). In some embodiments, the bone graft material is suitable for implantation into a human subject (e.g., retains a sufficient amounts of native cells to promote osteogenesis at the site of implantation).

B. Subject

In some embodiments, the recipient of the bone graft material is a human subject. In some embodiments, the recipient of the bone graft material is a human subject having a bone defect or bone fracture. In some embodiments, the recipient of the bone graft material is a human subject having a spinal deformity or spinal injury. In some embodiments, the recipient of the bone graft material is a human subject having a dental deformity or defect. In some embodiments, the recipient of the bone graft material is the same as the donor. In some embodiments, the recipient of the bone graft material is different from the bone graft material donor. The subject receiving the bone graft material as an implant may be human or a non-human animal. Non-human animals include non-human primates, rodents, canines, felines, porcines, bovines, equines, ovines, and the like.

IV. Methods and Systems of Manufacturing

In one aspect, the present disclosure provides a method of manufacturing a bone graft material. In some embodiments, the method comprises combining a radiopaque component with a cancellous bone component to produce the bone graft material. In some embodiments, the bone graft material optionally comprises a binder, an additive, demineralized cortical bone, or a combination thereof.

Turning now to the drawings, FIG. 1 depicts aspects of an exemplary technique for producing a bone graft material, according to embodiments of the present disclosure. As shown here, a demineralized cortical bone component 110 can be combined with a non-demineralized cortical bone component 120 to produce a combined cortical bone component 130. The combined cortical bone component 130 can be combined with a processed cancellous bone component 140 to produce a cellular bone graft material 150. In some embodiments, a binder 190 can be combined with the demineralized cortical bone 110, the non-mineralized cortical bone 120, the combined cortical bone 130 or the processed cancellous bone 140 prior to forming the cellular bone graft material 150.

In some embodiments, the demineralized cortical bone component 110, the non-demineralized cortical bone component 120, and the processed cortical bone component 140 can be obtained from the same deceased donor.

According to some embodiments, the demineralized cortical bone component 110 can include ribbons or particles such as those described in U.S. patent application Ser. No. 15/431,309, U.S. Patent Publication No. 2017/0035937, and U.S. Pat. No. 9,486,556, the contents of which are incorporated herein by reference. In some cases, the demineralized cortical bone component 110 can include particles such as those described in U.S. Patent Publication Nos. 2014/0255489 and 2017/0035937, the contents of which are incorporated herein by reference. In some instances, the demineralized cortical bone component 110 can be referred to as the matrix of the cellular bone graft material 150. In some instances, the demineralized cortical bone component 110 can be present at 50% (w/w) of the cellular bone graft material 150.

According to some embodiments, the non-demineralized cortical bone component 120 can be present in powder form. In some instances, the non-demineralized cortical bone component 120 can be present at 10% (w/w) of the cellular bone graft material 150. In some cases, the non-demineralized cortical bone component 120 can be present in particulate form, and the particles can have a diameter within a range from 100 microns to 4 mm. In some embodiments, the non-demineralized cortical bone component 120 functions to provide, among other things, an amount of radiopacity to the cellular bone graft material 150. In some embodiments, the non-demineralized cortical bone component 120 can be replaced by or supplemented with another radiopaque component. Exemplary radiopaque components include, for example, non-demineralized cortical bone, barium sulfate, bismuth trioxide, bismuth subcarbonate, tungsten, titanium, zirconium oxide, iodinated polyesters or iodinated aliphatic monomers.

As depicted in FIG. 1, the demineralized cortical bone component 110 and the non-demineralized cortical bone component 120 can be added together to produce a combined cortical bone component 130. In some cases, the combined cortical bone component 130 can be produced by mixing the demineralized cortical bone component 110 and the non-demineralized cortical bone component 120 together. Any of a variety of mixing, stirring, or tumbling techniques can be used to achieve this result. For example, the demineralized cortical bone component 110 and the non-demineralized cortical bone component 120 can be placed into an orbital shaker and mixed therein. In some cases, the demineralized cortical bone component 110 and the non-demineralized cortical bone component 120 can be placed into a vessel or container and mixed with a Resodyn LabRAM ResonantAcoustic® Mixer (Resodyn Acoustic Mixers, Inc., Butte, Mont.) or a similar resonant acoustic vibration device or high intensity mixing device. Exemplary related mixing techniques are disclosed in U.S. Patent Publication No. 2017/0035937, the content of which is incorporated herein by reference.

According to some embodiments, the processed cancellous bone component 140 can include cancellous bone obtained from donor-derived vertebral bodies, ileum, or long bones. In some cases, the processed cancellous bone component 140 can include cancellous bone obtained from donor-derived Gerdy's tubercle on the proximal metaphysis of the tibia. In some embodiments, the cancellous bone can be present in the form of cubes, spheres, irregularly shaped granules, or other particles or particle shapes, as well as solid constructs made of demineralized bone. In some cases, the processed cancellous bone can be present in the form of ground chips, with a particle size range between 10 µm and 10 mm. In some cases, the cancellous bone can be present in the form of ground chips, with a particle size range between 200 µm and 7 mm, 500 µm and 5 mm, 1 mm and 4 mm, and 300 µm and 2 mm.

Cancellous bone from a deceased donor bone tissue can be recovered and modified with a demineralization protocol, a decellularization protocol, or both a demineralization protocol and a decellularization protocol, to obtain the processed cancellous bone component 140. In some embodiments, cancellous bone from a deceased donor bone tissue can be recovered, and modified with a non-enzymatic process (e.g. passive soaking, or eluting) that removes erythrocytes (red blood cells) and other immunogenic or unwanted elements from the cancellous bone, while blood-derived mesenchymal stem cells (MSCs) remain intact and adhered to the cancellous bone.

In some instances, the processed cancellous bone component 140 can be present at 20% to 90% (w/w) of the bone graft material 150. In some embodiments, the cancellous bone can be present at any of 30% to 80% (w/w), 40% to 60% (w/w), 20% to 40% (w/w), 20% to 50% (w/w), and 40% to 90% (w/w) of the bone graft material.

In some instances, the bone graft material 150 may include cortical ribbons at 20-80% (w/w) of the final composition such as, for example, 20%, 25%, 30%, 35%, 40%, 45%, 50%, 55%, 60%, 65%, 70%, 75%, or 80% (w/w) of the final composition. In some instances, the bone graft material 150 may include processed cancellous at 10-70% (w/w) of the final composition such as, for example, 10%, 15%, 20%, 25%, 30%, 35%, 40%, 45%, 50%, 55%, 60%, 65%, 70%, (w/w) of the final composition. In some instances, the bone graft material 150 may include non-demineralized cortical bone powder at 1-20% (w/w) of the final composition such as, for example, 1%, 2%, 3%, 4%, 5%, 6%, 7%, 8%, 9%, 10%, 11%, 12%, 13%, 14%, 15%, 16%, 17%, 18%, 19%, or 20% (w/w) of the final composition. For example, the bone graft material 150 can include cortical ribbons at 50% (w/w) of the final composition, processed cancellous at 40% (w/w) of the final composition, non-demineralized cortical bone powder at 10% (w/w) of the final composition, or a combination of any thereof.

According to some embodiments, the demineralized cortical bone component 110, the non-demineralized cortical bone component 120 or other radiopaque material, and the processed cancellous bone component 140 can be combined directly. According to some embodiments, the demineralized cortical bone component 110 and the processed cancellous bone component 140 can first be combined together, and then that combination can be combined with the non-demineralized cortical bone component 120 or other radiopaque material. According to some embodiments, the non-demineralized cortical bone component 120 or other radiopaque material and the processed cancellous bone 140 can first be combined together, and then that combination can be combined with the demineralized cortical bone component 110.

In some cases, a passive soaking protocol can involve placing the cancellous bone in a container of cell culture media, such as Minimum Essential Media (MEM), for a period of time. In some cases, the passive soaking can be from 2-60 minutes. In some cases, the passive soaking can be 5 minutes or 10 minutes. In some cases, the passive soaking can be 20 minutes or 30 minutes. In some cases, the media is Minimum Essential Medium Eagle but other suitable media are known in the art. In some cases, the media is supplemented with a serum such as fetal bovine serum (FBS), for example at 5-10%. In some cases, the media is supplemented with Human Platelet Lysate (hPL). In some cases, the media can include an anticoagulant, such as ACD-A Anticoagulant Citrate Dextrose Solution, Heparin, Solution A (Citra Labs, Braintree, Mass.). In some cases, the media can include a material that degrades DNA, such as deoxyribonuclease or DNase. The volume of media used to soak the cancellous bone may depend on the amount of cancellous bone being processed. For example, 100 grams of ground cancellous can be soaked in 200-300 ml of media. In some cases, the passive soaking protocol is performed at room temperature (e.g., approximately 25° C.). In some cases, the passive soaking protocol is performed at a temperature between 4° C. and 37° C. In some cases, the passive soaking protocol is performed at 37° C. The passive soaking protocol can be performed as a "standing still" soak or rinse, where the cancellous bone is place in the media, and then the media is poured off. In some cases, the passive soaking protocol can include any number of desired soaking cycles (e.g. 1-5, or more soaking cycles). In some embodiments, the bone graft material comprises between 1% and 20% cell culture media. In one embodiment, the bone graft material comprises between 5% and 20% cell culture media. In another embodiment, the bone graft material comprises between 10% and 16% cell culture media.

In some cases, the cancellous bone is not treated with active rinsing or shaking, as these steps may remove or compromise blood-derived mesenchymal stem cells (MSCs) adhered or attached to the cancellous bone. In some cases, the cancellous bone is not treated with sonication, as sonication may remove or compromise blood-derived mesenchymal stem cells (MSCs) adhered or attached to the cancellous bone.

In some embodiments, the cancellous bone is not subjected to, or treated with, any growth protocols, culturing protocols, expansion protocols, passaging protocols, or the like. As such, the cancellous bone can be prepared directly from bone from a donor, for example by milling and/or grinding. Any suitable method of milling or grinding cancellous bone may be used to produce the cancellous bone component. Exemplary grinding or milling protocols are disclosed in U.S. Patent Publication No. 2012/0258178, the contents of which are incorporated herein by reference.

In some embodiments, the cancellous bone can be present at 20% to 90% (w/w) of the bone graft material. In some embodiments, the cancellous bone can be present at 30% to 80% (w/w), 40% to 60% (w/w), 20% to 40% (w/w), 20% to 50% (w/w), and 40% to 90% (w/w) of the bone graft material. In some embodiments, the cancellous bone can be present at 30% to 80% (w/w), 40% to 60% (w/w), 20% to 40% (w/w), 20% to 50% (w/w), and 40% to 90% (w/w) of the bone graft material.

Figure 2:
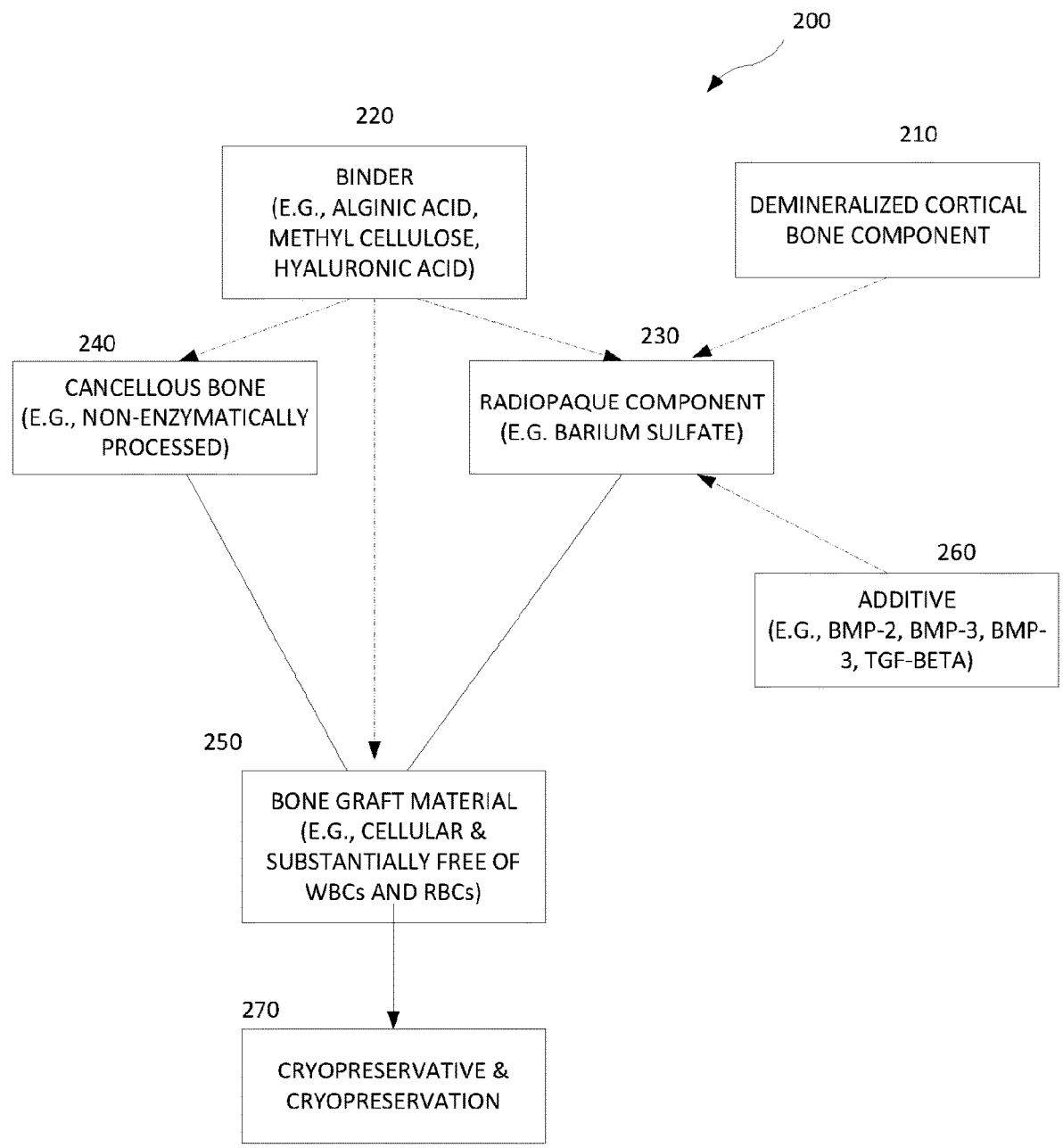
FIG. 2 depicts aspects of another process for manufacturing bone graft material according to an exemplary embodiment of the disclosure.

FIG. 2 depicts aspects of another exemplary technique for producing a bone graft material, according to embodiments of the present disclosure. As shown here, a radiopaque component 230 can be combined with cancellous bone 240 to produce a bone graft material 250.

In some embodiments, the cancellous bone 240 and the radiopaque component (e.g., non-demineralized cortical bone) 230 are obtained from the same deceased donor.

According to some embodiments, the cancellous bone component 240 can include non-enzymatically processed cancellous bone. In some embodiments, cancellous bone can be present in the form of cubes, spheres, irregularly shaped granules, or other particles or particle shapes, as well as solid constructs made of demineralized bone. In some cases, cancellous bone can be present in the form of ground chips, with a particle size range between 10 µm and 10 mm. In some cases, the cancellous bone can be present in the form of ground chips, with a particle size range between 200 µm and 7 mm, 500 µm and 5 mm, 1 mm and 4 mm, and 300 µm and 2 mm.

In some embodiments, cancellous bone from a donor can be recovered and modified with a demineralization protocol, a decellularization protocol, or both a demineralization protocol and a decellularization protocol, to obtain the cancellous bone component 240. In some embodiments, cancellous bone can be recovered from a donor and modified with a non-enzymatic process (e.g. passive soaking, or eluting) that removes erythrocytes, leukocytes, and other immunogenic elements from the cancellous bone, while blood-derived mesenchymal stem cells (MSCs) remain intact and adhered or attached to the cancellous bone.

In some instances, the cancellous bone 240 can be present at 20% to 90% (w/w) of the bone graft material 250. In some embodiments, the cancellous bone 240 can be present at 30% to 80% (w/w), 40% to 60% (w/w), 20% to 40% (w/w), 20% to 50% (w/w), and 40% to 90% (w/w) of the bone graft material 250.

According to some embodiments, the radiopaque component 230 can be present in powder form. In some instances, radiopaque component can comprise non-demineralized cortical bone present at 10% (w/w) of the bone graft material 250. In some cases, the radiopaque component (e.g., non-demineralized cortical bone) can be present in particulate form, and the particles can have an average diameter within a range from 100 microns to 4 mm. In some embodiments, the non-demineralized cortical bone component functions to provide, among other things, an amount of radiopacity to the cellular bone graft material 250. In some embodiments, the non-demineralized cortical bone component can be replaced by or supplemented with another radiopaque component 230 such as barium sulfate, bismuth trioxide, bismuth subcarbonate, tungsten, titanium, zirconium oxide, iodinated polyesters or iodinated aliphatic monomers.

As depicted in FIG. 2, the cancellous bone 240 and the radiopaque component 230 can be added together to produce a bone graft material 250. In some embodiments, the bone graft material 250 can be produced by mixing the cancellous bone 240 and the radiopaque component 230 together. Any of a variety of mixing, stirring, or tumbling techniques can be used to achieve this result. For example, the cancellous bone component 240 and the radiopaque component 230 can be placed in a flask on an orbital shaker and mixed therein. In some cases, the cancellous bone 240 and the radiopaque component 230 can be placed into a vessel or container and mixed with a Resodyn LabRAM ResonantAcoustic® Mixer (Resodyn Acoustic Mixers, Inc., Butte, Mont.) or a similar resonant acoustic vibration device or high intensity mixing device. Exemplary related mixing techniques are disclosed in U.S. Patent Publication No. 2017/0035937.

According to some embodiments, the bone graft material 250 can comprise a demineralized cortical bone component 210, which can include ribbons and/or particles such as those described in U.S. patent application Ser. No. 15/431,309, U.S. Patent Publication No. 2017/0035937, and U.S. Pat. No. 9,486,556. In some cases, the demineralized cortical bone component 210 can include particles such as those described in U.S. Patent Publication Nos. 2014/0255489 and 2017/0035937. In some instances, the demineralized cortical bone component 210 can be present in an amount up to 50% (w/w) of the bone graft material 250. In some embodiments, the demineralized cortical bone component can be combined with the radiopaque component, prior to combining the radiopaque component with the cancellous bone component.

According to some embodiments, the bone graft material 250 can comprise a binder 220, which improves handling and cohesiveness properties of the bone graft material, as compared to bone graft materials lacking the binder. In some embodiments, the binder 220 can include one or more of alginic acid, methyl cellulose, hyaluronic acid, gelatin, polaxamer, polyvinyl alchol (PVA), polyvinylpyrrolidone (PVP), polylactic acid (PLA), polyglycolide (PG), carboxymethyl celluose, chitosan, chitin, or a metal salt of any thereof. The metal salt may be an alkali metal salt or an alkaline earth metal salt. In some embodiments, the binder 220 can be present at 0.5% to 50% (w/w) of the bone graft material 250. In some embodiments, the binder 220 can be present at 1% to 25% (w/w) of the bone graft material 250. In some embodiments, the binder 220 can be present at 2% to 10% (w/w) of the bone graft material 250. In some embodiments, the binder 220 can be present at 1% to 5% (w/w) of the bone graft material 250. In some embodiments, the binder 220 can be present at 10% to 25% (w/w) of the bone graft material 250. In some embodiments, the binder 220 can be present at 20% to 40% (w/w) of the bone graft material 250. In some embodiments, the binder 220 can be present at 30% to 50% (w/w) of the bone graft material 250. In some embodiments, the binder can be present at 4% (w/w) of the bone graft material 250. In some embodiments, the binder can be combined with the cancellous bone or the radiopaque component prior to combining of the radiopaque component with the cancellous bone component.

According to some embodiments, the bone graft material 250 can comprise an additive 260, which promotes osteogenic properties of the bone graft material, as compared to bone graft materials lacking the additive. In some embodiments, the additive 260 can comprise a bone morphogenic protein (BMP), fibroblast growth factor-2 (FGF-2), insulin-like growth factor I (IGF-I), insulin-like growth factor II (IGF-II), platelet derived growth factor (PDGF), transforming growth factor beta I (TGFβ-I) or vascular endothelial growth factor (VEGF). In some embodiments, the additive 260 is a native or endogenous cell of a component of the bone graft material (e.g., cancellous bone). In some embodiments, the additive is a BMP (e.g., BMP-2). In some embodiments, the additive is a recombinant BMP. Any suitable method of preparing recombinant BMPs for use with a bone graft may be used. Exemplary recombinant BMPs are disclosed in U.S. Pat. Nos. 5,849,880 and 7,300,772, the contents of which are incorporated herein by reference in their entireties. In some embodiments, the additive can be present at 0.5% to 50% (w/w) of the bone graft material 250. In some embodiments, the additive can be present at 1% to 25% (w/w) of the bone graft material 250. In some embodiments, the additive can be present at 2% to 10% (w/w) of the bone graft material 250. In some embodiments, the additive can be present at 1% to 5% (w/w) of the bone graft material 250. In some embodiments, the additive can be present at 4% (w/w) of the bone graft material 250.

As depicted in FIG. 2, the bone graft material can be subjected to cryopreservation to allow for long term storage of the bone graft material at sub-zero temperatures. Any suitable cryopreservation method may be used to produce the bone graft material. Exemplary cryopreservation protocols are disclosed in U.S. Pat. Nos. 5,071,741; 8,367,059; 8,460,860; 9,192,695; 9,808,558; 9,814,803; and U.S. Patent Publication No. 2012/0258178, the contents of which are incorporated herein by reference.

As depicted in FIG. 2, the cancellous bone 240 and radiopaque component 230 can be combined together to produce a bone graft material 250. Any of a variety of mixing techniques can be used to achieve this result. In one embodiment, the cancellous bone and the radiopaque component can be placed in a flask and mixed (e.g., using an orbital shaker).

In some embodiments, the bone graft material is prepared by combining a radiopaque component with a cancellous bone component, wherein the cancellous bone component comprises osteoreparative cells; hydrating a binder in a cell culture media for about 5 minutes to about 60 minutes to form a hydrated binder; and combining the hydrated binder with the radiopaque component and the cancellous bone component to form the bone graft material, wherein the bone graft material has an average cell count of between 1,000 to 50 million osteoreparative cells per gram of bone graft material. In some instances, the cancellous bone component comprises ground cancellous bone (cancellous bone powder). In some instances, the radiopaque component is cortical bone. In some instances, the cortical bone is ground cortical bone (cortical bone powder). In some instances, the binder is alginic acid (also referred to as alginate). In some instances, the cell culture media is serum free.

In one embodiment, the bone graft material is prepared by combining non-demineralized cortical bone with cancellous bone, wherein the cancellous bone contains osteoreparative cells; hydrating alginic acid in cell culture media (e.g., 4% (w/v) alginic acid) for a period of time (e.g., 30 minutes) to form hydrated alginic acid; and combining the hydrated alginic acid with the non-demineralized cortical bone and cancellous bone to form the bone graft material, wherein the bone graft material comprises 10% non-demineralized cortical bone (w/w) and 70% cancellous bone (w/w), and wherein the bone graft material has an average cell count of between 1,000 to 50 million MSCs per gram of bone graft material. In some instances, the cell culture media is serum free. In some instances, the hydrated alginic acid may be 4% (w/v) alginic acid in DMEM. In some instances, the hydrated alginic acid, the non-demineralized cortical bone, and the cancellous bone are mixed to homogeneity to form the bone graft material. In some instances, the bone graft material is formed into a specific three-dimensional shape such as, for example, a sphere or a cube. In some instances, the bone graft material is then cryopreserved.

In some cases, the bone graft components can be packaged by scooping different components without mixing or stirring or shaking, but by laying the bone graft components together in a container. For example, it is possible to load a spoon or spatula with a predetermined amount of the respective constituents, so as to provide the desired quantity of a bone graft material. The individual components of the cellular bone graft material can be layered (e.g. one above the other) into the container, with no mixing. For example, with respect to FIG. 1, a 10 cc product can include 5 cc of bone ribbons at the bottom, 4 cc of cancellous bone and 1 cc of non-demineralized cortical powder, layered and packaged without mixing. The process of combining the cortical bone component 130 and the processed cancellous bone component 140 should operate to retain blood-derived mesenchymal stem cells (MSCs) which are adhered or attached to the cancellous bone. For example, with respect to FIG. 2, a 10 cc product can include 9 cc of cancellous bone at the bottom, and 1 cc of a radiopaque component, layered and packaged without mixing. The process of combining the cancellous bone 240 and the radiopaque component 230 should operate to retain native osteoreparative cells, such as MSCs which are adhered or attached to the cancellous bone 240.

Any of a variety of quality control or assay techniques can be performed on the bone graft material 150. For example, quality control can be achieved through MSC recovery by trypsin 160, or other currently known methodologies such as cellular out-growth after final processing to obtain a cell count of CD90+ and other mesenchymal stem cell markers. In some instances, quality control can be achieved by performing an enzymatic release protocol (e.g. using an enzyme such as trypsin, collagenase, neutral proteases or lipase) followed by a flow cytometry protocol to assess cell surface markers (e.g., CD90, CD105, and/or CD73). See, e.g., Bara et al., *Stem Cells*, (2014), 32:1713-1723 and Boxal and Jones, *Stem Cell International* (2012), 1-12 (DOI: 10.1155/2012/975871), both of which are incorporated herein by reference in their entireties. Relatedly, quality control can involve placing an explant culture of processed cancellous bone for cellular out-growth on a petri dish with culture media, followed by cell surface labeling with the appropriate antibodies (e.g., as discussed herein) followed by measurement via flow cytometry.

Optionally, an assay, for example an Alkaline Phosphatase (ALP) assay 170, such as the assay described by Calvi et al., *Nature*, 425, 841-846 (2003), can be performed to evaluate or demonstrate the functional integrity of the cancellous bone having adhered or attached MSCs. For example, metabolic assays such as MTT or Presto Blue® may be used (discussed below). In some instances, commercially available alkaline phosphatase substrate kits (e.g., Vector Laboratories, Burlingame, Calif. or BioVision, Inc., Milpitas, Calif.) can be used for alkaline phosphatase (ALP) analysis to detect living cells in the bone graft material (or a component thereof) (see, Examples 8, 9, and 11 herein).

According to some embodiments, other ex-vivo assays, such as a chick embryo chorioallantoic membrane (CAM) assay 180, or a modified CAM assay (such as the assay described in Moreno-Jimenez et al., *Sci. Rep.*, (2016)), can be used to evaluate or demonstrate the functional integrity of the cancellous bone having native MSCs remaining attached to the cancellous bone.

C. Cryopreservation

In some embodiments, the bone graft material undergoes cryopreservation to allow for long-term storage at subzero temperatures, such as −80° C. or −196° C. Any suitable method of cryopreservation may be used to cryopreserve the bone graft material. Examples include methods set forth in U.S. Pat. Nos. 5,071,741; 8,367,059; 8,460,860; 9,192,695; 9,808,558; 9,814,803; and U.S. Provisional Application 62/618,000 filed Jan. 16, 2018, entitled "cryopreservation of cartilage and osteochondral tissue", all of which are incorporated herein by reference in their entireties.

In some embodiments, the bone graft material or an individual component of the bone graft material (e.g., cortical bone or cancellous bone) can be individually cryopreserved. In some embodiments, cryopreservation includes incubating, bathing, or soaking the bone graft material with a cryopreservation solution containing a cryoprotectant. In some embodiments, the cryopreservation solution is a buffer or cell culture media comprising one or more cryoprotectants. In some embodiments, the cryoprotectant comprises dimethyl sulfoxide (DMSO), CS10®, trehalose, dextrose, alpha-tocopherol, stabilized ascorbic acid, resveratrol methanol, butanediol, propanediol, glycerol, hydroxyethyl starch, a glycol, or a combination thereof. In some embodiments, the glycol comprises ethylene glycol, polyethylene glycol, propylene glycol, or butylene glycol. In some embodiments, the cryoprotectant is DMSO. In some embodiments, the cryoprotectant solution comprises two or more cryoprotectants as opposed to a single-agent cryoprotectant. In some embodiments, the cryoprotectant solution comprises DMSO and alginate. In some embodiments, the alginate is a sodium salt alginate.

In some embodiments, a cryoprotectant is added to a bone graft material such that the final concentration of cryoprotectant, for example, in a buffer or cell culture media, is between 1% and 40% (vol/vol). In some embodiments, a cryoprotectant is added to the bone graft material such that the final concentration of cryoprotectant is between 5% and 30% (vol/vol). In some embodiments, a cryoprotectant is added to the bone graft material such that the final concentration of cryoprotectant is between 10% and 20% (vol/vol).

In some embodiments, the cryoprotectant solution is provided in a volume of between 10 ml and 2,500 mL. For example, the cryopreservation solution may be 10 mL, 20 mL, 30 mL, 40 mL, 50 mL, 60 mL, 70 mL, 80 mL, 90 mL, 100 mL, 200 mL, 300 mL, 400 mL, 500 mL, 600 mL, 700 mL, 800 mL, 900 mL, 1 L, 1.1 L, 1.2 L, 1.3 L, 1.4 L, 1.5 L, 1.6 L, 1.7 L, 1.8 L, 1.9 L, 2.0 L, 2.1 L, 2.2 L, 2.3 L. 2.4 L, 2.5 L, or another volume within the range of 10 mL to 2,500 mL. In some instances, the volume of the cryopreservation solution is limited by the capacity of the vessel used to cryopreserve the bone graft material (e.g., a 1 L flask).

Generally, it is preferred that the cryoprotectant is added to a bone graft material in a final concentration in which native or endogenous cells of the bone graft material are not materially affected (e.g., killed) due to toxicity of the cryoprotectant. In some embodiments, the final concentration of cryoprotectant does not result in more than 10% toxicity to the number of total cells in the bone graft material. In some embodiments, the final concentration of cryoprotectant does not result in more than 20%, 30%, 40%, 50%, 60%, 70%, 80% or 90% toxicity to the number of total cells in the bone graft material. In some embodiments, the final concentration of cryoprotectant in the cryopreservation solution results in less than 80%, 70%, 60%, 50%, 40%, 30%, 20%, or less than 10% toxicity to the total number of cells present in the bone graft material.

In one embodiment, the cryopreservative solution comprises 10% DMSO. In some embodiments, the cryopreservation solution may contain from 5% to 40% cryoprotectant, or a combination of cryoprotectants in a buffer or cell culture medium. In some instances, the cryopreservation solution may comprise serum (e.g., human serum) or platelet rich plasma (e.g., human platelet lysate), or both, and one or more cryoprotectants. For example, the cryoprotectant solution may comprise a cell culture medium containing 5%-40%, 10%-30%, or 5-20% DMSO. In some embodiments, the cryopreservation solution can comprise 5%, 10%, 15%, 20%, 25%, or 30% DMSO. In some instances, where a plurality of cryopreservation solutions are used in the cryopreservation process, the cryopreservation solutions can include different amounts (e.g., concentrations) of DMSO to be used at different points in the cryopreservation process.

In some embodiments, the cryoprotectant is applied to the bone graft material by incubating, soaking, or agitating (e.g., using an orbital shaker) the bone graph material with a cryopreservation solution (e.g., cell culture media containing the cryoprotectant) for a period of time such that the cryoprotectant coats and/or enters cells of the bone graft material. In some embodiments, the bone graft material is incubated with a cryoprotectant solution for at least 2 minutes to 4 hours. For example, the bone graft material may be soaked for 2 min, 5 min, 10 min, 15 min, 20 min, 25 min, 30 min, 40 min, 50 min, 60 min, 75 min, 90 min, 120 min, 180 min, 200 min, 220 min, or a period of time otherwise less than 4 hours. In some embodiments, the bone graft material is incubated with a cryoprotectant solution for between 5 and 60 minutes. In some instances, the bone graft material may be incubated with the cryoprotectant solution at room temperature or at refrigerated temperatures (e.g., 4° C.). In some embodiments, the bone graft material can be agitated on an orbital shaker, a rocker, or a stir plate (e.g., with a magnetic stirrer in a vessel containing the bone graft material and cryopreservation solution), while being incubated. In some embodiments, the bone graft material can be sonicated while soaked in the cryopreservation solution (continuously, for a portion of the soaking period, or intermittently during the soaking period). In some embodiments, a semi-dry cryopreservation step is performed, wherein the cryoprotectant solution is decanted from the bone graft material after incubation with the cryoprotectant solution and prior to rate controlled freezing. An example of this method is shown in Example 12. In some embodiments, the bone graft material after incubation in the cryoprotectant solution is patted dry before rate controlled freezing. In some embodiments, the cryoprotectant solution is decanted from the bone graft material after incubation with the cryoprotectant solution (i.e., semi-dry cryopreservation) and the bone graft material is patted dry before rate controlled freezing.

In some embodiments, a wet cryopreservation step is performed, wherein after incubation of the bone graft material in the cryoprotectant solution, the bone graft material is frozen in the cryoprotectant solution via rate controlled freezing An example of this method is shown in Example 1).

In some embodiments, the bone graft material can be frozen using dry ice, liquid nitrogen or refrigeration to produce frozen bone graft material. Once frozen, the frozen bone graft material can be stored at subzero Celsius temperatures until desired, preferably at −80° C. or below (e.g., −196° C.).

In some embodiments, the cryopreservation solution may be removed or drained from the bone graft material prior to freezing. In some embodiments, an additional cryopreservation solution can be applied to the drained bone graft material, prior to freezing, and the additional cryopreservation solution can be incubated with the bone graft material for an appropriate period of time. Generally, the incubation period of bone graft material with any cryopreservation solution is a period of time that is less than one cell-cycle or passage of a native osteoreparative cell present in the bone graft material.

In some embodiments, the cryopreservation solution comprises a cell culture media. In some embodiments, the cell culture media is mammalian cell culture medium. In some embodiments, the cell culture media is nutrient free or can be supplemented with one or more essential nutrients. In some embodiments, the cell culture media comprises Dulbecco's Modified Eagle Medium (DMEM), Minimal Essential Media (MEM), Minimal Essential Media Eagle (MEME), or Complete Mesenchymal Stem Cell Media (e.g., Catalog No: M5566 from CellBiologics.com). In some embodiments, the cell culture media comprises a supplement. Exemplary supplements include Fetal Bovine Serum (FBS), Human Serum, Human Serum Albumin, and Human Platelet Lysate (hPL). In some embodiments, the cell culture media can include an antibiotic. In some embodiments, the antibiotic may be one or more of vancomycin HCl, gentamicin sulfate, polymyxin B sulfate, ciprofloxacin HCl, amphotericin B, bacitracin.

MEM is based on an earlier formulation of Basal Medium Eagle (BME) media. MEM is available with Earle's salts for use in a $CO_2$ incubator, or with Hanks' salts for use without $CO_2$. It is available in powder or liquid form. MEM contains no proteins, lipids, or growth factors and therefore requires supplementation, commonly with 10% Fetal Bovine Serum (FBS). MEM is commercially available from a number of manufacturers (e.g., ThermoFisher Scientific).

FBS is a by-product of the dairy industry originating from the blood of a bovine fetus. FBS contains growth factors and other proteins and is therefore used to supplement in vitro cell culture media. Typically, cells of interest (e.g., osteoreparative or MSCs) are incubated in cell culture media and a supplement (e.g., FBS) and after one or more passages, the cell culture media containing FBS is removed from the material of interest.

Human Serum Albumin (HSA) is found in human blood and is the most abundant protein in blood plasma. HSA is encoded by the ALB gene and is typically used as a supplement in cell culture media. HSA has also been utilized for cell washing and for cryopreservation. HSA can be obtained from human blood or may be prepared "animal-free", for example, using plants to recombinantly express HSA.

Human Platelet Lysate (hPL) is a supplement for cell culture media. It is a liquid obtained from human blood platelets after several freeze/thaw cycles. hPL is commercially available from a number of manufacturers (e.g., Mill Creek Life Sciences).

In some embodiments, bone graft material prepared according to the methods disclosed herein can be incubated, soaked or bathed in a cell culture medium for a time that is less than one cell-cycle or passage of a native osteoreparative cell in the bone graft material (e.g., MSCs or osteoblasts). In some embodiments, the bone graft material is incubated in a cell culture medium and native osteoreparative cells present in the bone graft material are not passaged in vitro. In some embodiments, the bone graft material is incubated in a cell culture medium and the native osteoreparative cells in the bone graft material do not undergo a population doubling in vitro. Generally, it is preferred that native osteoreparative cells of the bone graft material are not expanded or passaged in vitro but are instead implanted at a desired site in a subject (e.g., at a bone defect or within a spinal cage), and that the native osteoreparative cells undergo population doubling in the recipient (e.g., in vivo).

In some embodiments, the cryopreserved bone graft material is thawed on ice, at room temperature, or at 37° C. for at least 10 minutes prior to implantation into a subject. Preferably, the frozen bone graft material is thawed on ice, at room temperature, or at 37° C. for between 10 and 60 minutes prior to implantation into a subject. In some embodiments, once thawed, the bone graft material retains at least 10%, 20%, 30%, 40%, 50%, 60%, 70%, or more, native osteoreparative cells as compared to the pre-cryopreservation bone graft material. In some instances, the bone graft material retains at least 10%, 20%, 25%, 30% 40%, 45%, 50%, 55%, 60%, 65%, 70%, 75%, 80%, 85%, 90% or 95% cell viability, after freezing and thawing, as determined by cell count of the bone graft material before and after cryopreservation of the bone graft material. In one example, the cryopreserved bone graft material retains at least 20% cell viability as compared to the bone graft material before cryopreservation.

The bone graft material can be assessed for native or viable cells. For example, the viability of cells in the bone graft material may be assessed metabolically using reagents such as Presto Blue® reagent or MTT. In some instance, Trypan Blue® can be used to assess cell viability. In some instances, the bone graft material is frozen for a period of time (such as one week), then thawed, and assessed for cell viability. Any suitable method to determine the presence of live cells in the bone graft material can be used. Exemplary methods, include those set forth in US Patent Publication Nos: 2014/0093480; 2016/0290994; U.S. Pat. No. 8,163,495, and Examples 8, 9 and 11, herein.

D. Evaluation of Bone Graft Material

In some instances, the bone graft material is evaluated before and/or after cryopreservation to evaluate at least one characteristic of the bone graft material. In some embodiments, evaluation may be performed to determine the presence and/or absence of one or more native cells (e.g., leukocytes) in the bone graft material. In some embodiments, evaluation may be performed to determine the presence and/or absence of one or more native osteoreparative cells (e.g., MSCs) in the bone graft material. In some embodiments, evaluation may be performed to determine the mineral content (e.g., calcium) of the bone graft material. In some embodiments, evaluation may be performed to determine the presence and/or quantitation of one or more osteoreparative cell (e.g., osteocytes) in the bone graft material. In some embodiments, evaluation may be performed to determine the presence and/or absence of red and/or white blood cells in the bone graft material. In some embodiments, evaluation may be performed to determine the absence and/or quantitation of CD45+ cells in the bone graft material. In some embodiments, evaluation may be performed to determine the absence and/or quantitation of CD4+ cells in the bone graft material. In some embodiments, evaluation may be performed to determine the absence and/or quantitation of CD3+ cells in the bone graft material. In some embodiments, evaluation may be performed to determine the presence and/or quantitation of CD44+ cells in the bone graft material. In some embodiments, evaluation may be performed to determine the presence and/or quantitation of CD90+ cells in the bone graft material. In some embodiments, evaluation may be performed to determine one or more handling or cohesiveness properties of the bone graft material. Any suitable methods to determine one or more characteristics set forth above, may be used. Exemplary methods include flow cytometry, cell surface marker antibody binding, hemocytometer cell counting, and any of the methods disclosed in the Examples herein.

E. Cell Viability

In some embodiments, determining or evaluating cell viability of the bone graft material can include assessment of a metabolic activity of cells within the bone graft material. For example, cell viability can be measured using reagents such as PrestoBlue® or 3-(4,5-dimethylthiazol-2-yl)-2,5-diphenyltetrazolium bromide (MTT). The MTT cell viability assay is a method for determining live cell numbers in a test sample using a colorimetric plate reader. In another example, cell viability can be determined using a Cell Counting Kit 8 (CCK-8) assay. The CCK-8 assay is a colorimetric assay for the determination of the number of viable cells. The reagent in the CCK-8 assay is WST-8 [2-(2-methoxy-4-nitrophenyl)-3-(4-nitrophenyl)-5-(2, 4-disulfophenyl)-2H-tetrazolium, monosodium salt], which is reduced by dehydrogenases in living cells to produce a yellow colored product (formazan), that is soluble in cell culture medium. Accordingly, the amount of the formazan dye generated by the activity of dehydrogenases in living cells is directly proportional to the number of living cells in the test sample.

In some embodiments, cell viability can be evaluated after the bone graft material has been frozen for a period of time (e.g., 1 week, 1 month, 1 year, or up to 5 years). The frozen bone graft material can be thawed and evaluated for cell viability. In some embodiments, cell viability can include assessing the number or percentage of MSCs present in the thawed bone graft material. In some embodiments, the percentage of MSCs in the bone graft material (as a percentage of total cell composition of the bone graft material) is at least 5%. In some embodiments, the percentage of MSCs in the bone graft material (as a percentage of total cell composition of the bone graft material) is at least 10%, 20%, 30%, 40%, 50%, 60%, 70%, 80%, or more. In some embodiments, the percentage of MSCs in the bone graft material as a percentage of total cell composition of the bone graft material is between 5% and 30%. For example, cells expressing a MSC cell surface marker (e.g., CD44+ and CD90+) can be identified by the use of specific antibodies and flow cytometry (see, Example 4, herein). It will be readily apparent that any suitable method for determining or evaluated the presence and/or quantitation of live cells in bone graft material can be used.

F. Molding

In some embodiments, bone graft material of the present disclosure can be machined or molded into a desired shape, size, or applied to an existing surgical construct (e.g., a spinal cage) prior to implantation into a subject. The bone graft material can be prepared into shapes such as, but not limited to, spheres, cones, columns, wedges, pyramids, disks, cubes, and strips. In some embodiments, the bone graft material can be molded or prepared as an irregular shape. In some embodiments, the bone graft material retains its size and shape during the implantation procedure (e.g., for example during irrigation of the implantation site after implantation). In some embodiments, the bone graft material possesses a putty-like consistency and thus can be readily molded into any desired shape or size.

V. Methods of Treatment

In one aspect, the present disclosure provides a method for treating a subject with a bone graft material. In some embodiments, the method comprises administering a bone graft material to the subject, wherein the bone graft material comprises a radiopaque component and a cancellous bone component. In some embodiments, the bone graft material comprises an osteoreparative cell. In some embodiments, the bone graft material comprises native osteoreparative cells.

In some embodiments, the bone graft material is administrated to the subject to repair a bone defect or bone fracture. For example, a bone defect may be the result of cancer, hereditary disease, age-related bone loss (e.g., osteoporosis), trauma (e.g., injury), infection, and the like. Use of the bone graft material can be implemented in industries related to orthopedics, reconstructive surgery, dentistry, and podiatry. In some instances, the bone graft material may be reabsorbed and replaced with the patient's natural bone upon healing. In some instances, the bone graft material is retained in a subject after implantation, replacing the missing or damaged bone. The bone graft material may also have reconstructive applications, for example, in the context of missing sections of bone (such as surgical removal of cancerous bone). In some instances, the bone graft material of this disclosure provides tailored treatment options in terms of shape, size, and composition for treating a wide array of bone defects. In some instances, the bone graft material may be used for post-traumatic reconstructive cosmetic uses. The treatment methods are generally performed by a medical professional, such as a surgeon.

In some embodiments, the bone graft material is administrated to the subject during an orthopedic or neurosurgical procedure. In some embodiments, the orthopedic or neurosurgical procedure is a spinal fusion. In some embodiments, the bone graft material can be administered by molding and placing the bone graft material directly into a site of implantation (e.g., a bone cavity or defect). In some embodiments, the bone graft material can be administered to the subject by molding and placing the bone graft material into a surgical construct (e.g., a spinal cage), and placing the surgical construct into a site of implantation (e.g., vertebrae). In some instances, the bone graft material may be contacted with a saline solution, an antibiotic, cell culture media, or a combination thereof, prior to administering to the subject. In some embodiments, the bone graft material is hydrated or rehydrated with an appropriate solution (e.g., saline or alginic acid) to form a gel, gum, or putty-like consistency prior to implantation into the recipient.

In some embodiments, the bone graft material can be administered to a subject as a flowable, syringeable, putty-like material. For example, a putty-like moldable material can be delivered through a cannula or other syringe attachment to the defect site (see, for example U.S. patent application Ser. No. 13/712,295, the entire content of which is incorporated herein by reference for all purposes). A putty-like composition can possess improved handling and cohesiveness characteristics as opposed to bone graft materials of a powder or liquid form. For example, putty-like compositions may stay in place upon implantation. Relatedly, putty-like compositions may persist at the site of the application (e.g., bone defect area) and resist removal by irrigation and/or contact with blood.

The bone graft material described herein is useful for implantation into a subject having a defective site. The defective site may be a degenerated or damaged spinal disc, a bone defect, an oral defect, or a maxillofacial defect. The bone graft material described herein can be used to replace damaged, removed, or degenerated bone. The bone graft material can comprise a native osteoreparative cell that is therapeutic to healing the defective site by promoting bone growth (i.e., osteogenesis). In some instances, the bone graft material can comprise MSCs derived from the donor of the bone graft material. The terms "patient" and "subject" are used interchangeably herein.

Provided herein are methods of treating a bone defect in a subject, wherein the method of treatment includes administering to the subject a bone graft material at a bone defect site (also referred to herein as implantation site) in the subject. The bone defect site can include a degenerated or damaged spinal disc, an oral defect, and a maxillofacial defect. As used herein, oral and maxillofacial defects include defects in the head, neck, face, jaws, and the hard and soft tissues of the oral (mouth) and maxillofacial (jaws and face) region. Exemplary bone defects include damaged, diseased, degenerated, or missing bones. For example, the bone defect site may be a long bone, a short bone, a flat bone, an irregular bone, an intervertebral disc, or a portion of any of these bones. The subject may be a human or a non-human animal such as, for example, a non-human primate, a rodent, a dog, a cat, a horse, a pig, a cow, a bird, and the like. In some instances, the subject is a human.

In some instances, an exemplary method of treatment includes providing a bone graft material for the implantation site. This step may be performed following an evaluation of the patient. In some cases, a medical professional evaluates a subject to determine the nature of the bone defect that requires treatment and the bone graft material appropriate to treat the subject. In some instances, this process may include medical imaging, such as X-ray imaging, MRI scans, or CT scans, which provide dimensions of the bone defect site, and may be utilized for determining the desired configuration (such as size and/or shape) of the bone graft material. The appropriate bone graft material may comprise a native osteoreparative cell to promote bone growth and healing at the bone defect site. For example, an osteogenic bone graft material may be appropriate to treat a bone defect.

In some instances, the bone graft material may be shaped by the medical professional to be compatible with the configuration and/or dimensions of the implantation site. It is contemplated that the bone graft material may be shaped such as by cutting, bending, folding, and the like. For example, the bone graft material may be trimmed, for example with a surgical tool such as a scalpel or scissors, to fit into a bone defect site. In some instances, this step may include hydrating or rehydrating the bone graft material, for example with appropriate media or solution (e.g., saline or alginic acid).

In some embodiments, the bone graft material is administered to the implantation site of the subject. In some embodiments, the bone graft material may be implanted into, or within, a bone defect site. For example, an osteogenic graft may be implanted into a bone defect site in which the native bone is missing (whether through damage, disease, or surgical removal). In some embodiments, the bone graft material may be molded and inserted into a surgical construct such as a spinal cage, and the surgical construct is sutured or affixed with fasteners (such as screws) at the implantation site.

In some instances, when the bone graft material is implanted in a subject, the bone graft material may act as a stable physical support structure at the implantation site, replacing or supporting damaged, removed, or degenerated bone. In some instances, when the bone graft material is contained within a surgical construct (e.g., a spinal cage) and implanted in a subject, the bone graft material may act as a stable physical support structure at the implantation site, replacing or supporting damaged, removed, or degenerated bone.

VI. Kits

The methods and compositions of the present disclosure may be provided in one or more kits. The kits may include bone graft material or individual components necessary to prepare the bone graft material (e.g. a radiopaque component and a cancellous bone component), and instructions for use. Optionally, such kits may further include any additional components (e.g., recombinant BMPs or osteoreparative cells, such as MSCs) described in relation to the present disclosure and any other materials or items relevant to the present disclosure (e.g., a cryopreservation solution, for example containing DMSO and alginic acid). The instructions for use can also set forth any of the methods described herein.

EXAMPLES

Example 1: Exemplary Protocol for Preparing Bone Graft Material

The following is an exemplary protocol for preparing bone graft material as described herein.

Cancellous bone was produced by trimming cortical bone and cartilage away from the proximal and distal epiphysis and metaphysis of long bones using a band saw, and cutting the resulting cancellous bone blocks into roughly 2 cm$^2$ sized pieces. The cancellous bone was passed, using a single pass, through a Fortios Bone Mill outfitted with a XXXF cylinder blade (Spierings Tissue Processing B.V., Netherlands). The resulting ground cancellous bone was collected and transferred to a disposable flask. The ground cancellous bone was washed three (3) times in a 2 L disposable Erlenmeyer flask with 1 L of mammalian media (DMEM-F12) containing antibiotics (vancomycin HCl, gentamicin sulfate, amphotericin B, polymyxin B sulfate, ciprofloxacin HCl) using a 70 RPM orbital shaker platform at 37° C. for a period of 10 minutes per wash. The mammalian media was decanted between washes.

Next, non-demineralized cortical bone powder (e.g., non-demineralized cortical bone component) was prepared from cortical bone segments by grinding the cortical bone to approximately 500-1,000 μm using a Fitz Grinder, followed by size sieving.

The bone graft material was formulated by combining 90 grams of cancellous bone as prepared above, with 10 grams of non-demineralized cortical bone component, as prepared above.

The bone graft material can be packaged as 1 CC, 1.5 CC, 5 CC, 10 CC, or 15 CC units suitable for spinal cages or other orthopedic procedures, for example using AlloStem Jars and sieve inserts by weight. Cryopreservative (e.g., 90% Fetal Bovine Serum (FBS) and 10% dimethyl sulfoxide (DMSO)) was added to each jar and a rate controlled freezing (−1° C./min) was performed to −80° C. using ProChondrix cryo-jars. The frozen cryopreserved bone graft material was then stored, ready for later use.

Figure 3:
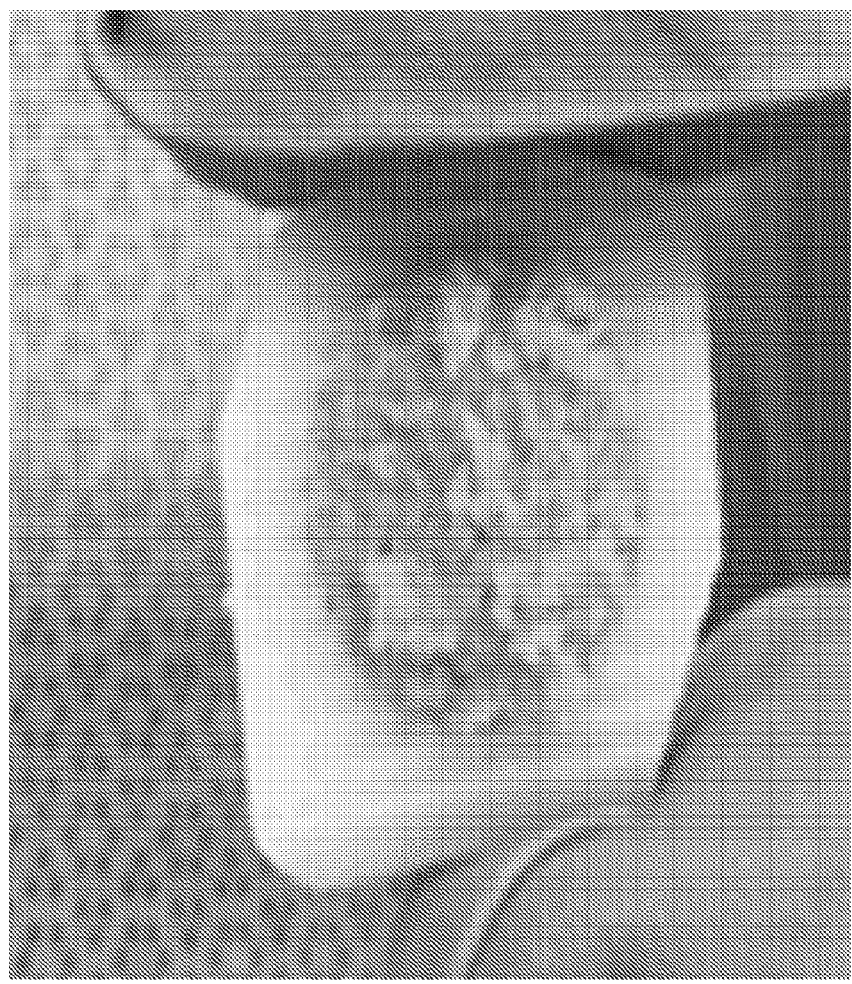
FIG. 3 is an image of a bone graft material of the disclosure positioned within a spinal cage.

Once thawed, the bone graft material can be molded and placed into spinal cages or other bone cavities to facilitate bone repair and growth (See, FIG. 3). The bone graft material was found to mold easily and retained its molded shaped, even while the spinal cage was manipulated by surgical staff for insertion into a subject. The handling consistency of the bone graft material resembled a putty or paste-like material.

Example 2: Radiopaque Properties of the Bone Graft Material

The bone graft material described herein may be observed, for example, by X-rays, due to its radiopaque properties. For example, once the bone graft material is inserted into a bone cavity, bone defect, or other surgical instrument (e.g., a spinal cage) the bone graft material may be used to aid potential repositioning of the surgical instrument, or monitoring of bone repair in the subject.

Here, a range of 0% to 20% non-demineralized cortical bone component was included in the bone graft material prepared essentially as described in Example 1 to demonstrate radiopaque properties of the bone graft material. An X-ray of the bone graft material was produced using standard clinical settings (see, Hauser and Cukla, *J. Prolotherapy*, (2009), 1(1):22-28.

Figure 4:
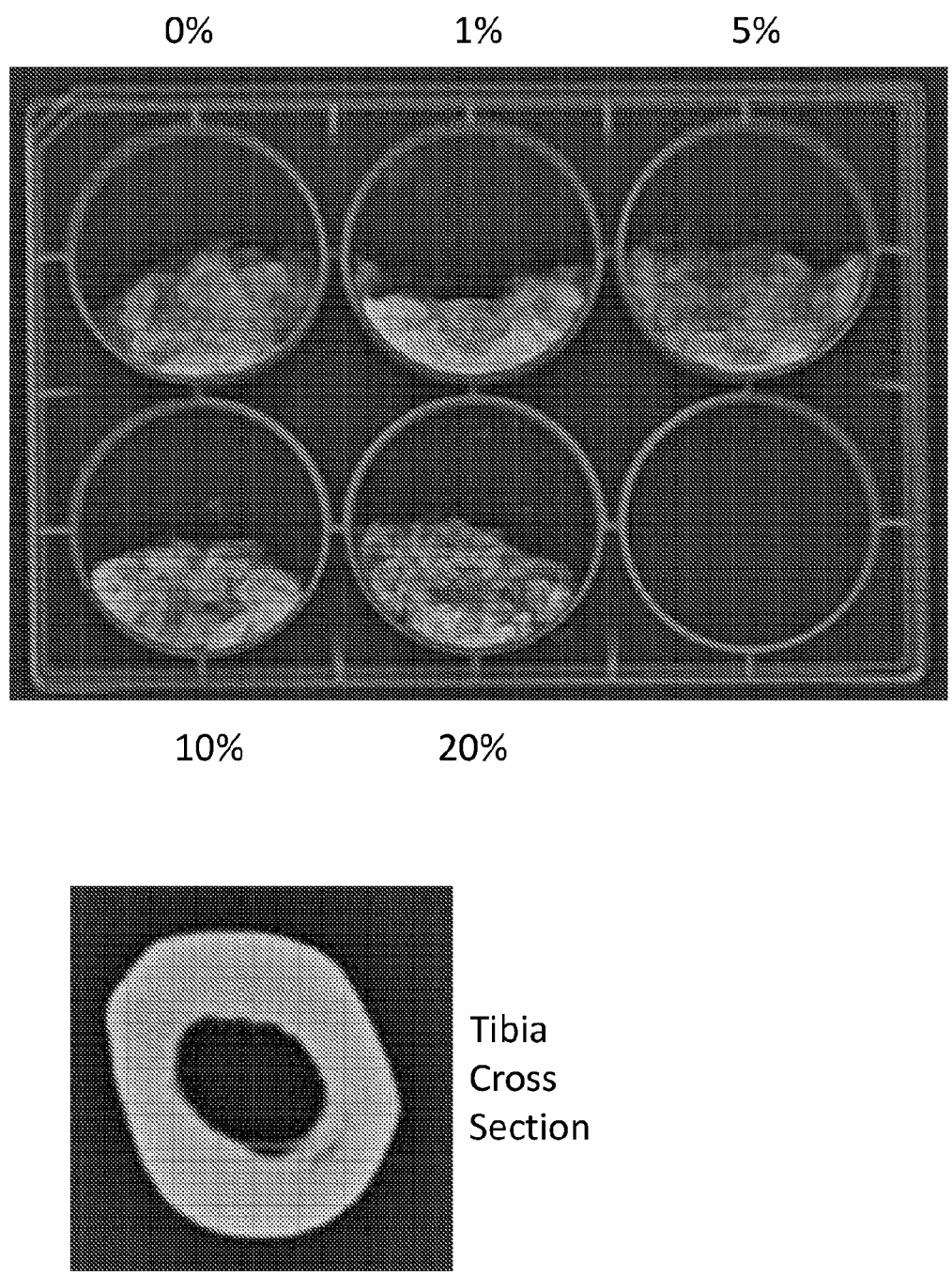
FIG. 4 is an image of an X-ray of exemplary bone graft materials of the disclosure containing different amounts of a radiopaque component (e.g., non-demineralized cortical bone component).

FIG. 4 illustrates the effect of non-demineralized cortical bone concentration on the detection of the bone graft material. While the bone graft material containing 0% non-demineralized cortical bone powder (top left image) was visible, the bone graft material became increasingly opaque with increasing concentrations of non-demineralized cortical bone powder in the bone graft material. Thus, a formulation containing 90% ground cancellous bone and 10% non-demineralized cortical bone was found to provide good X-ray imaging without compromising the handling and cohesive properties of the bone graft material.

Example 3: Cellular Viability of the Bone Graft Material

One impediment of prior allograft bone graft materials is that the bone graft material is processed to such an extent that all or substantially all immunogenic elements from the bone graft material are removed to avoid an immune system response once the bone graft material is implanted in the subject (e.g., GVHD). In doing so, the bone graft material often lacks osteogenic properties. A bone graft material that retains one or more endogenous cell populations that provides osteogenic properties would be particularly useful to facilitate bone graft repairs.

Collagenase may be used to detach endogenous cells from native tissue matrixes. However, collagenase alone is not efficient to release living cells from all tissue types. We therefore prepared various formulations of collagenase and collagenase/neutral proteases to determine which formulation(s) maintained cell viability of the bone graft material described herein.

Figure 5:
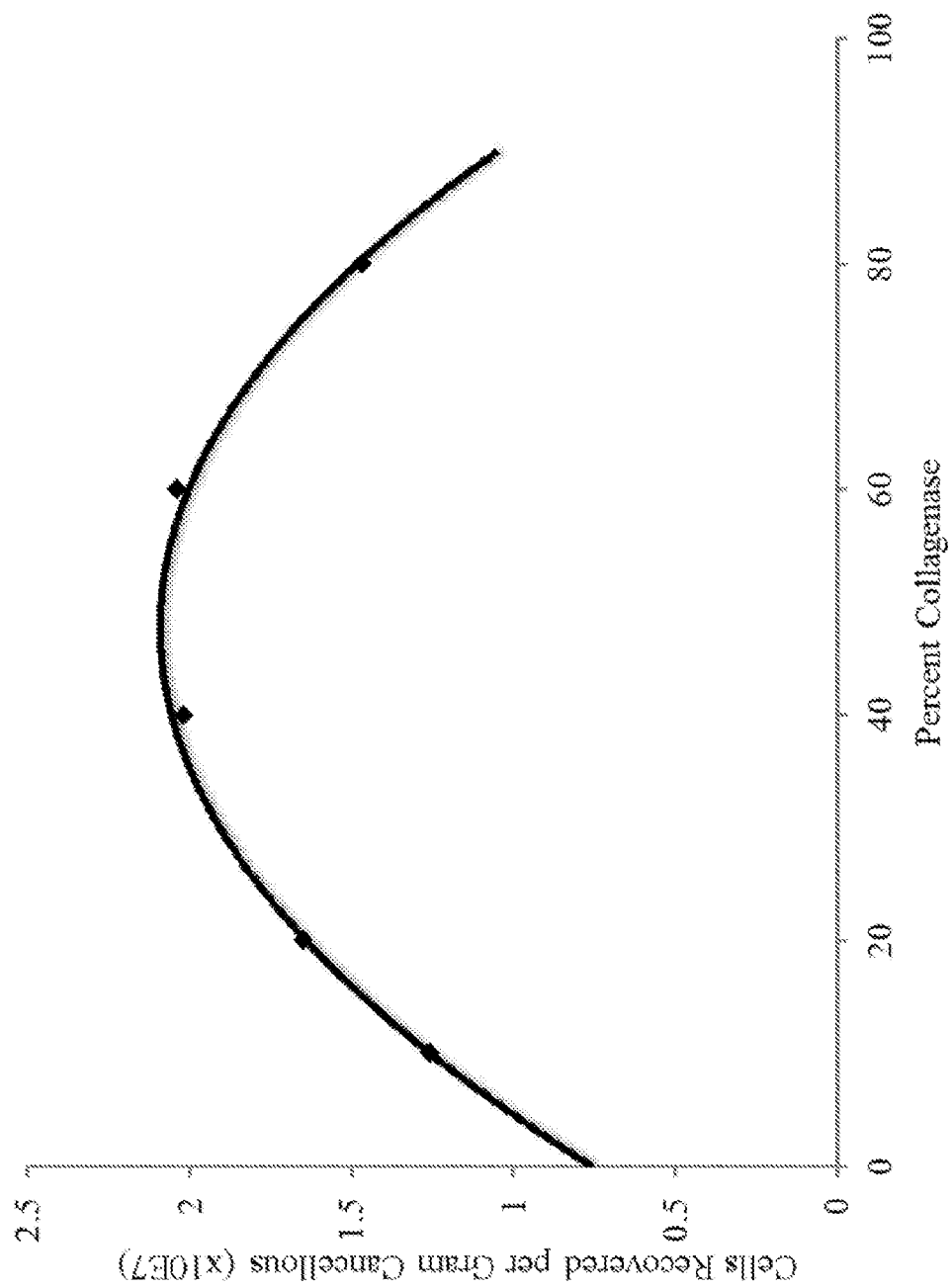
FIG. 5 is a graph showing total cell yield and recovery from exemplary bone graft materials of the disclosure using various collagenase preparations measured by flow cytometry. Maximum cell recovery was obtained using a 40% or 60% collagenase:40% neutral protease preparation. Approximately $2\times10^7$ cells per gram were recovered.

Formulations containing different concentrations of collagenase (0%-80%) and/or neutral proteases were evaluated for release of living cells from the bone graft material described in Example 1 (FIG. 5). Commercially available kits containing various proportions of collagenase and protease are readily available (for example, DE collagenase optimization kit from VitaCyte Collagenase IX (C9407) from Sigma Aldrich) was used as a control. All collagenase formulations were tested at a concentration of 1 mg/ml and placed in serum free growth medium at approximately 12.5 ml/gram bone graft material for 3 hours at 37° C. After the incubation period, viable cells detached from the bone graft material were counted using Trypan Blue staining (e.g., 1:1 cell dilution with staining and counting on a hemocytometer)

FIG. 5 provides the total cell yield for each collagenase formulation. VitaCyte DE40/400 and DE60/600 provided the highest yield of cells, approximately, $2.0 \times 10^7$ cells per gram of bone graft material. Based on these results, we selected DE60 with 60% collagenase: 40% neutral protease for use in subsequent studies.

Example 4: Characterization of Cells Present in the Bone Graft Material

The bone graft material facilitates bone repair upon placement into a bone cavity. This objective is fulfilled by providing a bone graft material that contains viable desirable living cells, such as Mesenchymal Stem Cells (MSCs), and limited quantities of undesirable cells (e.g., leukocytes and erythrocytes). In particular, residual white blood cells (i.e., cells that express the cell surface marker, CD45), pose a serious risk of immune system stimulation such as graft versus host disease (GVHD), when the bone graft material is implanted into an individual from whom the bone graft material is not derived (e.g., an allograft).

Using flow cytometry, we determined the types of cells present in the bone graft material described in Example 1 by releasing viable, living cells from the bone graft material using the collagenase formulation (DE60/600) described in Example 3.

After collagenase treatment of the bone graft material (i.e., cellular detachment), the cells were stained with antibodies to detect leukocytes and osteogenic cells (e.g., osteocytes and MSCs) and analyzed using an Acea NovoCyte instrument and NovoExpress Software. CD44+ serves as a cell surface marker for osteocytes; while CD90 serves as a primary cell surface marker for MSCs.

Flow cytometry evaluation of the bone graft material from Example 1 identified recoverable viable osteocytes (CD44+) and MSCs (CD90+, CD73+, CD105+, CD146+, Stro-1+, CD271+) (See, e.g., Bara et al., *Stem Cells*, (2014), 32:1713-1723; Hughes et al., *J. Bone Mineral Res.*, (1994) 9(1):39-44; and Nakashima et al., *Nat. Med.*, 17:1231-34), data provided in Table 1. Residual white blood cells (CD45+) were also detected from the bone graft material. While we expect to observe osteoblasts in the bone graft material, a representative cell surface marker has yet to be identified. As mentioned above, residual white blood cells (CD45+) may pose a health risk to the recipient of a bone graft due to an immunological response of the patient to the graft or from the graft to the patient (i.e., an allograft). Thus, limiting or removing CD45+ cells from the bone graft material is preferred. Table 1 provides a summary of the cell surface markers characterization and quantitated by flow cytometry of the bone graft material.

TABLE 1

Flow Cytometry Results

| Marker | Cell Type | Percent Positive | Total cells/gram bone graft material |
|---|---|---|---|
| CD45 | Leukocyte Common Antigen (an undesirable cell type) | 2.21 | 3.60E+05 |
| CD44 | Osteocyte | 63.6 | 1.04E+06 |
| CD90 | MSC | 8.78 | 1.43E+06 |
| CD73 | MSC | 9.18 | 1.50E+06 |
| CD105 | MSC | 0.74 | 1.21E+05 |
| Stro-1 | MSC | 3.42 | 5.57E+05 |
| CD146 | MSC | 0.07 | 1.14E+04 |
| CD271 | MSC | 3.07 | 5.00E+05 |
| | Average Number of cells | | $1.63 \times 10^7$ cells/gram bone graft material |

Example 5: Removal of Leukocytes from the Bone Graft Material

Mono-nucleated blood cells (leukocytes) are not desirable in the bone graft material and can be removed by washing the bone graft material according to the methods described herein. Here, the bone graft material was washed in serum-free Dulbecco's Modified Eagle Medium:Nutrient Mixture F12 (DMEM-F12) mammalian media (ThermoFisher Scientific, Catalog No.: 11330-099) at a ratio of 250 ml cold media per 100 grams of bone graft material. The washing cycle was performed at room temperature, on an orbital platform shaker set at 80 RPM, for a duration of 10 minutes. After washing, a cell counting flow cytometry procedure was performed to assess removal of leukocytes and to characterize the remaining cells in the bone graft material after each round of washing.

Figure 6:
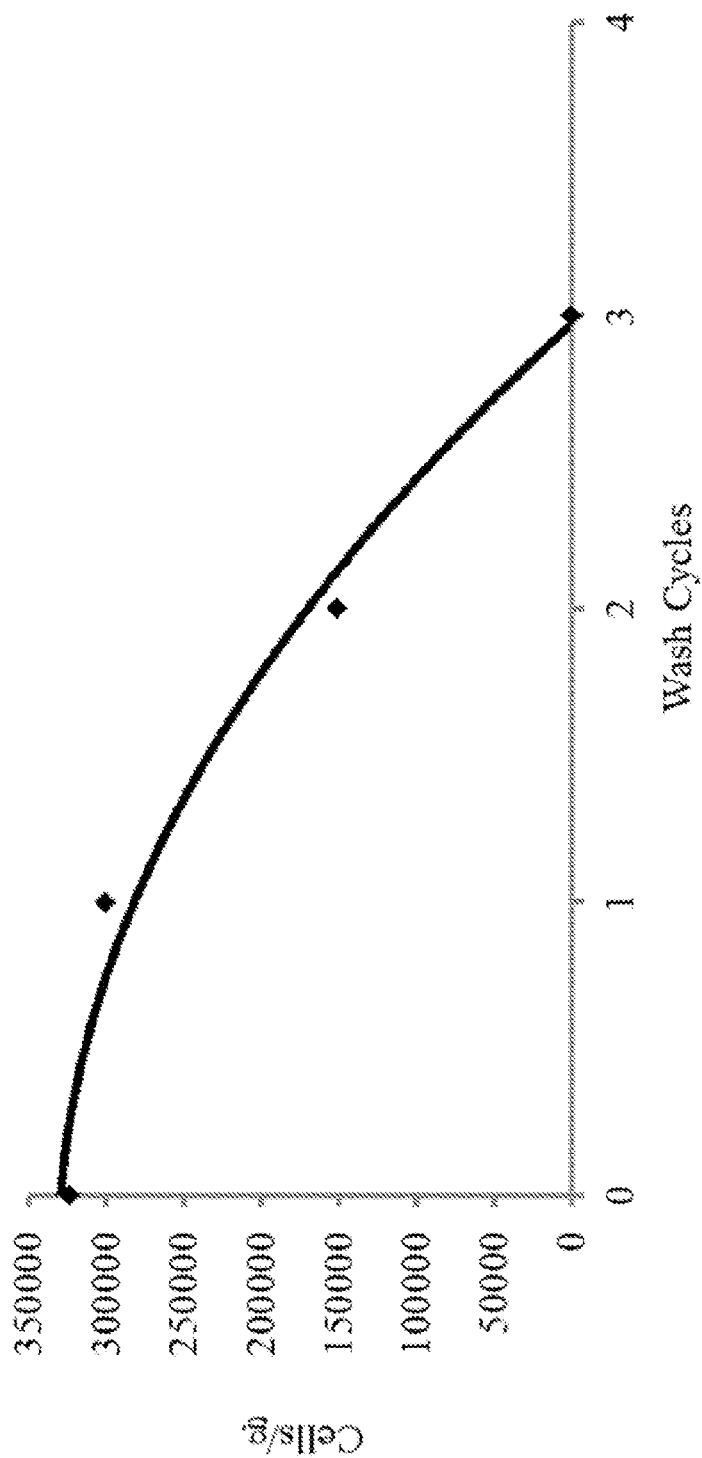
FIG. 6 is a graph showing reduction in CD45+ cells as a result of washing the exemplary bone graft materials of the disclosure. No CD45+ cells were detected in the exemplary bone graft material after three rounds of washing.

The results from the washing protocol are provided in FIG. 6, which indicated that three rounds of washing were sufficient to remove the leukocytes from the bone graft material. In this instance, no cells expressing CD45+(i.e., leukocytes) were detected after three rounds of washing.

A second study using bone graft material prepared from a different human donor was used to investigate the presence of T-cells in the bone graft material after washing. CD3 and CD4 are markers for T-cells, an immunogenic subset of leukocytes. CD4 is a marker for T-helper cells, monocytes, macrophages, and dendritic cells. Removal of these T-cell would improve the safety of the bone graft material by reducing or eliminating the risk posed by graft-versus-host disease (GVHD) complications. As can be seen from the data provided in Table 2, CD4+ cells were not detected in the bone graft material after the three washing cycles performed as described above for FIG. 6. In this instance, more than 97% of all leukocytes were removed from the bone graft material after three washes, and no CD4+ expressing cells were detected in the bone graft material after the three wash cycles.

TABLE 2

| Marker | Percent Positive | Cells/gram bone graft material |
|---|---|---|
| CD45 | 2.7 | 1.11E+05 |
| CD3 | 0.8 | 3.29E+04 |
| CD4 | 0.0 | 0 |

Example 6: Maintaining Osteogenic Properties of the Bone Graft Material

The washing protocol described in Example 5 did not significantly impact the osteogenic properties of the bone graft material. Here, trypan blue staining of cells present in the bone graft material was performed, followed by cell counting, and flow cytometry to determine the loss of osteogenic cells during the washing steps described in Example 5.

Figure 7:
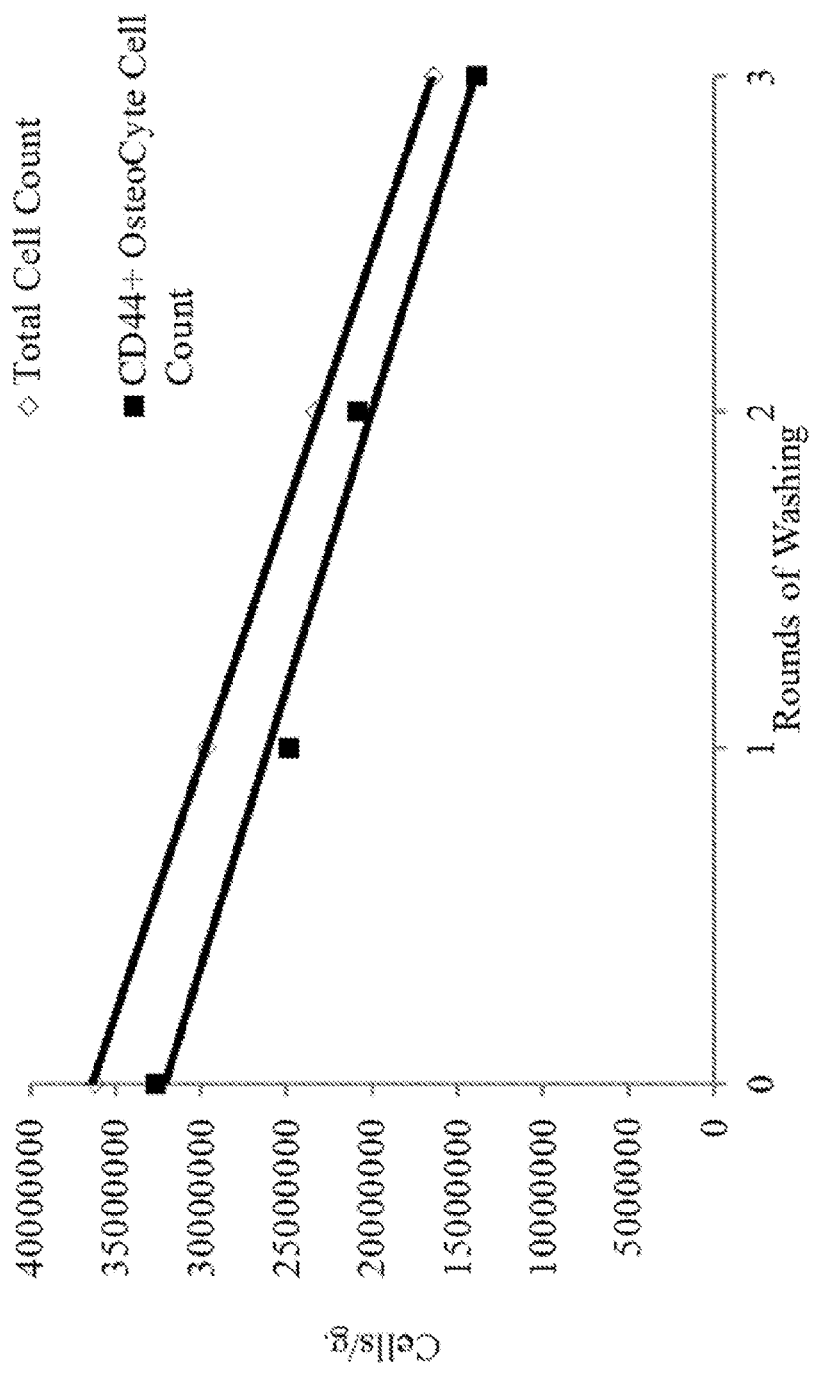
FIG. 7 is a graph showing limited reduction of osteogenic cells (e.g., osteocytes and MSCs) as a result of washing the exemplary bone graft materials. CD44+ cells were reduced at approximately the same rate as the number of total cells with each washing cycle.

FIG. 7 illustrates the concomitant loss of desirable cells (CD44+) with each round of washing. CD44+ cells were lost at approximately the same rate as total cells (e.g., CD44+, CD90+ and CD45+ cells) with each wash.

Figure 8:
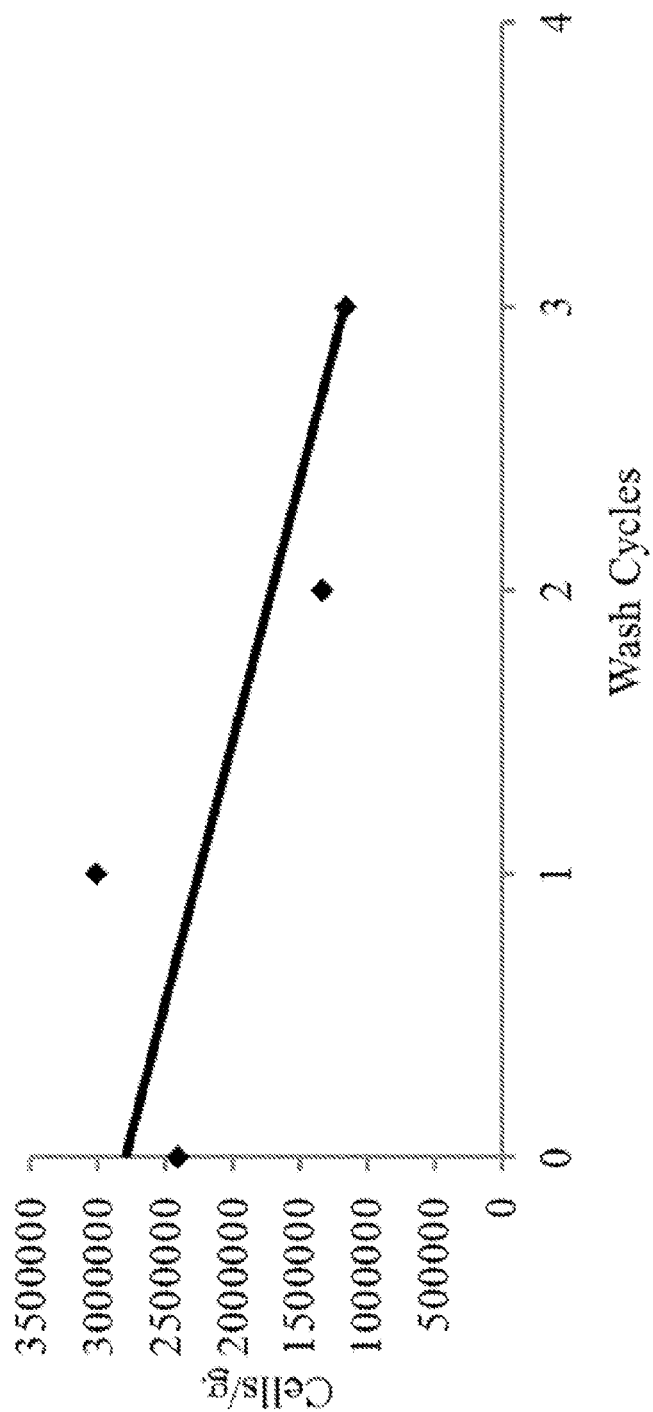
FIG. 8 is a graph showing limited reduction of mesenchymal stem cells (CD44+ and CD90+) as a result of washing the exemplary bone graft materials. CD44+ and CD90+ cells were reduced at a rate of approximately 17% per wash.

FIG. 8 illustrates the loss of mesenchymal stem cells (CD90+ cells) with each round of washing. Approximately 17% of the MSCs were lost with each round of washing. It was determined that three rounds of washing was appropriate to removing leukocytes from the bone graft material while retaining a maximal number of desirable cells, such as MSCs and osteocytes.

Example 7: Cellular Retention in Bone Graft Material from Six Distinct Donors

Using the trypan blue method already described (e.g., 1:1 cell dilution with staining and counting on a hemacytometer), we evaluated cellular retention of bone graft materials prepared from six different human donors. Each bone graft material was prepared essentially according to Example 1.

Overall, a significant number of desirable osteogenic cells were retained for each bone graft material prepared. The retention of cells in the bone graft materials ranged of 4.2 million cells per gram of bone graft material to 52 million cells per gram of bone graft material, with an overall mean of 19 million total cells per gram of bone graft material. MSCs represented an average of 10.7% of total cells in the bone graft material, with a mean MSC cell count of 1.7 million MSCs per gram of bone graft material.

Interestingly, two of the six donors tested were 57 years old. The two donors exhibited lower overall cell counts and lower stem cell counts (see, Table 3) as compared to the remaining four donors. Accordingly, we anticipate an age correlated decline in total cell number and MSCs per gram of bone graft material and therefore recommend that a maximum age of donors for bone graft material be 55 years of age or younger.

TABLE 3

| Donor | After wash total cells/gram | After wash osteocytes % CD44+ | After wash MSCs % CD44+ CD90+ | MSCs/gram bone graft material |
|---|---|---|---|---|
| NA | 5.2E+07 | 93.9 | 7.4 | 3.5E+06 |
| NA | 2.5E+07 | 85.4 | 10.9 | 2.5E+06 |
| 57M | 4.1E+06 | 29.9 | 14.5 | 5.4E+05 |
| NA | 1.1E+07 | no data | no data | no data |
| 23M | 1.6E+07 | 6.36 | 8.78 | 1.4E+06 |
| 57M | 4.2E+06 | 30.9 | 11.7 | 4.9E+05 |
| Mean #of cells | 1.9E+07 | 49.3 | 10.7 | 1.7E+06 |

Example 8: Recovery of Viable Cells from the Bone Graft Material after Cryopreservation and Thawing In order to maximize the number of viable cells retained in the bone graft material after cryopreservation and thawing, we evaluated various incubation times of the bone graft material in cryoprotectants. Here, we assessed incubation times from 10 to 60 minutes to allow for penetration of the cryoprotectant into the bone graft material prior to initiating a rate controlled freezing step.

Samples of the bone graft material were incubated at room temperature with 10% dimethyl sulfoxide (DMSO) in Fetal Bovine Serum (FBS), as the cryopreservative. The samples were incubated between 10 and 60 minutes before transferring to an isopropanol cryopreservation jar for freezing to −80° C. After the samples were frozen, and subsequently thawed to room temperature, cells in each sample were counted using a cell counter (e.g., Nexcelom CelloMeter instrument) and live and dead cells were stained or evaluated using a fluorescent alkaline phosphatase assay (BioVision K422-500) to detect living cells.

The results (provided in Table 4) indicated that a 10 minute incubation period in cryopreservative was sufficient to allow penetration of cryoprotectant into the bone graft material. Longer incubations with this particular formulation appeared to result in a loss of viable cells, likely due to DMSO toxicity.

TABLE 4

Cell viability and cell count due to variation
in cryopreservation incubation period

| Incubation Time | CelloMeter | | Alkaline Phosphatase Assay | Percent |
| --- | --- | --- | --- | --- |
| | Percent Viable | Cell count/gram | Cell count/gram | CD90+ cells (MSC) |
| 10 minutes | 57.1 | 1.27E+06 | 1.26E+06 | 69.56 |
| 30 minutes | 50.0 | 9.40E+05 | 1.03E+06 | 64.78 |
| 60 minutes | 42.8 | 1.01E+06 | 8.05E+05 | 59.82 |

The data from Table 4 indicates that while the total cell count per gram of bone graft material is not identical using the two different methods (e.g., Cellometer versus Alkaline Phosphatase assay), over 59% of all viable cells from the bone graft material were MSCs, even when 10% DMSO was present as the cryoprotectant for 60 minutes. For shorter incubations in 10% DMSO, the percentage of viable MSCs from the bone graft material reached almost 70%. Accordingly, a 10 minute cryopreservation process in 10% DMSO was considered sufficient for further studies.

Example 9: Optimization of Cryopreservation Reagents

In this Example, the concentration of DMSO in the cryopreservation solution was varied to determine an optimal concentration of cryoprotectant for the bone graft material, while maintaining a maximal number of desirable cells, (e.g., osteoreparative cells) in the thawed bone graft material.

Here, the concentration of DMSO in Fetal Bovine Serum (FBS) was modulated from 5% to 20% to assess the impact on post thaw cell viability. As in Example 8, CelloMeter live/dead cell enumeration and alkaline phosphatase assay were used to determine the post thaw cell counts of each bone graft material.

Figure 9:
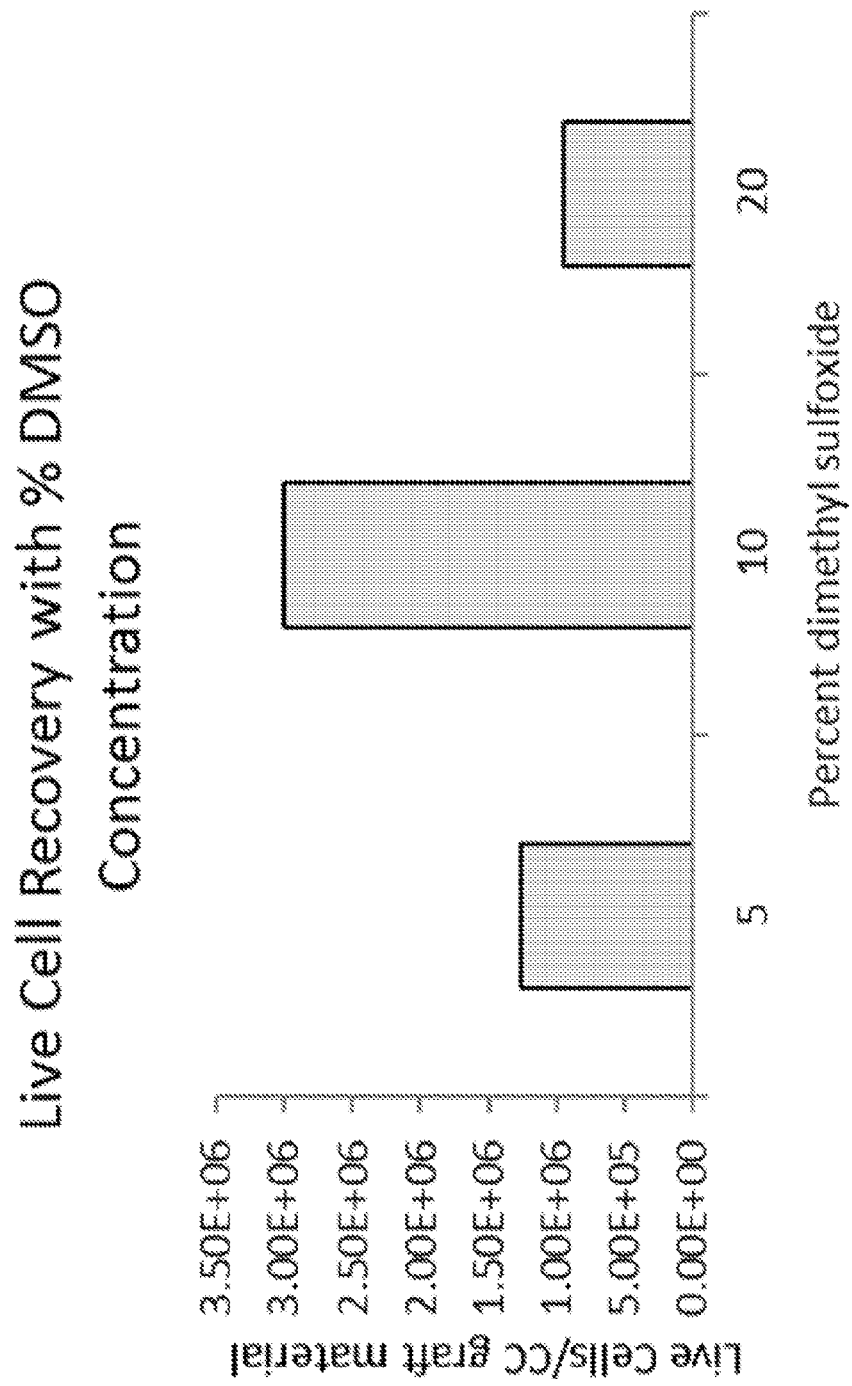
FIG. 9 is a graph showing the total cell of viable cells from exemplary bone graft materials as impacted by various concentrations of cryoprotectant.

The results are provided in FIG. 9 and indicate that 10% DMSO in FBS provides optimal post-thaw cell viability for the bone graft material.

Example 10: Detection of Endogenous Bone Morphogenic Proteins (BMPS) in the Bone Graft Material Bone Morphogenic Proteins (BMPs) are members of the TGF-β growth factor family and are known to actively stimulate bone growth (See, Linkhart et al., Bone, (1996) 19(1)1S-12S and Chen et al., Growth Factors, (2004) 22(4) 233-41). It is expected that bone graft materials containing detectable levels of one or more BMPs would be particularly useful to facilitate bone repair and growth after implantation in a subject.

Here, standardized Enzyme Linked ImmunoSorbent (ELISAs) from R&D Systems were utilized to quantitate BMP-2 (DBP200), BMP-4(DBP400), and BMP-7(DBP700) in the bone graft material prepared essentially according to Example 1. Data from demineralized cancellous bone, previously tested at AlloSource, is provided as a comparison. The results from the ELISA are provided in Table 5.

TABLE 5

| Growth Factor | Bone graft material pg/gram | Demineralized cancellous Bone pg/gram |
| --- | --- | --- |
| BMP-2 | 2450 | 110 |
| BMP-4 | 60 | Non-detectable |
| BMP-7 | 4291 | 5257 |

Similar levels of BMP-7 were detected in both the bone graft material and the demineralized cancellous bone (4291 versus 5257 pg/gram). However, both BMP-2 and BMP-4 was detected at higher levels in the bone graft material compared to the demineralized cancellous bone. While it is expected that BMP levels will vary from donor to donor, the bone graft materials of the instant disclosure contain significant and detectable levels of endogenous BMPs that are capable of facilitating new bone growth once implanted in a subject.

Example 11: Detection of Osteogenic Cells in the Cellular Bone Graft Material—a Qualitative Control Assay An assay was developed using BioVision Kit K422-500 to establish a qualitative alkaline phosphatase assay that could be used to measure the presence of living cells in the bone graft material, for example, to assay a batch of bone graft material for osteogenic cells prior to storage at −80° C. or post-thaw. This experiment was designed to detect alkaline phosphatase without the need for cell culture passage or extended culturing times. The bone graft materials were tested directly after thawing and detection of alkaline phosphatase in the bone graft material verified the presence of osteogenic cells in the bone graft material. In this experiment, three non-identical bone graft materials were tested (e.g., different donors).

The K422-500 fluorescence kit is useful for assays requiring high sensitivity. We observed signal saturation with dilute samples of the bone graft material because the viable cell count of the bone graft material is very high. However, acceptable results were obtained when using a 1:110 dilution of the bone graft material and a 5 minute incubation step. The results of the alkaline phosphatase assay to detect live cells is provided in Table 6.

TABLE 6

Cell Count Determined by Alkaline Phosphatase Assay

| Sample | 1 | 2 | 3 |
| --- | --- | --- | --- |
| Mean Signal 360 nm | 8966 | 15528 | 17727 |
| Calculated cells/gram of bone graft material | 476,919 | 825,960 | 942,943 |

A less sensitive assay (e.g., BioVision Kit K420-500) could also be utilized to determine the presence of osteogenic cells in a batch of bone graft material. Higher dilution's of the bone graft material (e.g., 1:200 or 1:500) may be useful for longer incubation times, and the combination of longer incubation times and increased dilution of the bone graft material may be necessary for some bone graft material. The standard curve regression was $R^2$=0.9934.

Example 12: Alternative Protocol for the Preparation of Cellular Bone Graft Material The following is an alternative exemplary protocol for preparing a bone graft material suitable for use as bone graft implant in a subject.

Cancellous bone was produced according to the method set forth in Example 1. Non-demineralized cortical bone powder (e.g., non-demineralized cortical bone component) was also prepared essentially as set forth in Example 1. Two different formulations were tested containing a binder, and assessed for improved handling and cell viability.

For Formulation A, 4 grams of sodium alginate powder was hydrated in 16 ml DMEM-F12 for 30 minutes to obtain a gel or gum consistency. Subsequently, the sodium alginate gum was added to 72% cancellous bone and 8% non-demineralized cortical bone to form a final concentration of 4% alginic acid. The three components were mixed well to form the bone graft material and molded into a desired shape (e.g., a sphere). The bone graft material was then incubated for 20 minutes in a cryopreservation solution of 10 ml FBS/10% DMSO before the bone graft material underwent rate controlled cryopreservation to −80° C. (e.g., using ProChondrix cryo-jars).

For Formulation B, 4 grams of sodium alginate powder was hydrated directly with 16 ml of the cryopreservation solution (FBS/10% DMSO) for 20 minutes to obtain a gel or gum consistency. Subsequently, the sodium alginate gum was added to 72% cancellous bone and 8% non-demineralized cortical bone to form a final concentration of 4% alginic acid, which had been soaked in the same cryopreservative solution (FBS/10% DMSO) for 5 minutes. The three components were mixed well to form the bone graft material and molded into a desired shape (e.g., a sphere). The bone graft material was then incubated for 10 minutes in the cryopreservation solution before undergoing a rate controlled freezing to −80° C.

Initially, two bone graft materials from different human donors were prepared for assessment. Formulations A and B were also tested in triplicate. The results are provided in Table 7.

TABLE 7

4% alginate pre-hydration and total cell viability/per CC bone graft material

|  | Formulation | Trial 1 | Trial 2 | Trial 3 | Average |
|---|---|---|---|---|---|
| Donor 1 without DMSO in alginate hydration | A | 3.95E+06 | 3.10E+06 | 3.98E+06 | 3.68E+06 |
| Donor 2 without DMSO in alginate hydration | B | 6.25E+06 | 8.32E+06 | 5.60E+06 | 6.72E+06 |
| Donor 2 with DMSO in alginate hydration | B | 6.81E+06 | 5.76E+06 | 9.05E+06 | 7.21E+06 |

As is evident from the data of Table 7, pre-hydrating the bone graft material with alginate (i.e., Formulation A) either in the presence or absence of a cryopreservative did not impact cell viability of the different bone graft materials.

Next, total cell viability and cell populations present in the bone graft material prepared via Formulation A were characterization both pre- and post-cryopreservation using cell staining and flow cytometry methods already disclosed herein. The results of which are shown in Table 8.

TABLE 8

4% Alginate, 20 min pre-hydration in 10% DMSO, 10CC, cryopreservation to −80° C.

| Source |  | Trial 1 | Trial 2 | Trial 3 | Mean | % of viable cells |
|---|---|---|---|---|---|---|
| Pre Cryo | total cells/gram | 3.95E+06 | 3.98E+06 | 3.10E+06 | 3.68E+06 | N/A |
| Osteocytes | % CD44 | 78.47 | 71.79 | 72.81 | 74.36 |  |
| MSCs | % CD90 | 17.22 | 23.97 | 14.77 | 18.65 |  |
| Leukocytes | % CD45 | 3.69 | 2.85 | 2.93 | 3.16 |  |
| Post Cryo | total cells/gram | 5.21E+05 | 1.06E+06 | 3.57E+05 | 6.46E+05 | 22.0% |
| Osteocytes | % CD44 | 20.88 | 17.65 | 19.6 | 19.38 |  |
| MSCs | % CD90 | 42.52 | 35.21 | 35.38 | 37.70 |  |
| Leukocytes | % CD45 | 3.55 | 3.00 | 2.57 | 3.04 |  |

As is evident from the date of Table 8, a cell viability percentage of 22% was obtained using Formulation A (the pre-hydration alginate formulation).

Overall, the percentage of osteocytes dropped between pre- and post-cryopreservation measurements by over 50% based on the total viable cell count. In contrast, the percentage of viable MSCs in the bone graft material increased between pre- and post-cryopreservation measurements by almost 100% when using the pre-hydrating alginate Formulation A.

Total cell viability of the bone graft material prepared via Formulation B was also characterized using a cryoprotectant solution incubation period of either 30 minutes or 60 minutes prior to rate controlled freezing, using the cell staining and flow cytometry methods disclosed herein. Additionally, a semi-dry cryopreservation method was also tested, wherein the cryoprotectant solution was decanted from the bone graft material after incubation (30 or 60 minutes) in the cryoprotectant solution and prior to rate controlled freezing.

Post-thaw cell viability of the bone graft material incubated in the cryoprotectant solution for 60 minutes, or incubated in the cryoprotectant solution for 60 minutes followed by semi-dry cryopreservation (i.e., decanting of the cryoprotectant solution from the bone graft material after incubation in the cryoprotectant solution), was found to result in at least a doubling of cell viability as compared to an incubation period of 30 minutes in cryoprotectant solution, with or without the semi-dry cryopreservation step.

All features of the described systems are applicable to the described methods mutatis mutandis, and vice versa. All features of the described compositions and/or kits are applicable to the described methods mutatis mutandis, and vice versa.

All patent filings, scientific journal articles, books, treatises, and other publications and materials discussed in this application are hereby incorporated by reference in their entirety for all purposes.

Where a range of values is provided, it is understood that each intervening value between the upper and lower limits of that range is also specifically disclosed, to the smallest fraction of the unit or value of the lower limit, unless the context clearly dictates otherwise. Any encompassed range between any stated value or intervening value in a stated range and any other stated or intervening value in that stated range is disclosed. The upper and lower limits of those smaller ranges may independently be included or excluded in the range, and each range where either, neither, or both limits are included in the smaller range is also disclosed and encompassed within the technology, subject to any specifically excluded limit, value, or encompassed range in the stated range. Where the stated range includes one or both of the limits, ranges excluding either or both of those included limits are also included.

It is to be understood that the figures and descriptions of the disclosure have been simplified to illustrate elements that are relevant for a clear understanding of the disclosure. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments, such substitution is considered within the scope of the disclosure.

The examples presented herein are intended to illustrate potential and specific implementations of the invention. It can be appreciated that the examples are intended primarily for purposes of illustration for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Aspects and embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

While exemplary embodiments have been described in some detail, by way of example and for clarity of understanding, those of skill in the art will recognize that a variety of modification, adaptations, alternate constructions, equivalents and changes may be employed. Hence, the scope of the present invention should be limited solely by the claims.

What is claimed is:

1. A method of manufacturing a bone graft material, the method comprising:
   combining a radiopaque component with a cancellous bone component to produce the bone graft material, wherein the cancellous bone component comprises native osteoreparative cells and less than 5% CD4+ cells, less than 5% CD3+ cells, and less than 5% CD45+ cells, and
   wherein the radiopaque component comprises particles having an average diameter from 100 microns to 4 mm, and the cancellous bone component comprises a particle size between 1 mm and 4 mm.

2. The method of claim 1, wherein the radiopaque component comprises one or more of non-demineralized cortical bone, barium sulfate, bismuth trioxide, bismuth subcarbonate, tungsten, titanium, zirconium oxide, iodinated polyesters, or iodinated aliphatic monomers.

3. The method of claim 1, further comprising combining a demineralized cortical bone component with the radiopaque component, prior to combining the radiopaque component with the cancellous bone component.

4. The method of claim 1, wherein the cancellous bone component comprises a non-enzymatically processed cancellous bone component.

5. The method of claim 4, wherein the non-enzymatically processing comprises a passive soaking cycle whereby the cancellous bone component is passively soaked in mammalian media.

6. The method of claim 1, further comprising combining a binder with (a) the cancellous bone component or (2) the radiopaque component prior to the combining of the radiopaque component with the cancellous bone component.

7. The method of claim 1, further comprising combining a binder with the radiopaque component and the cancellous bone component to produce the bone graft material.

8. The method of claim 6, wherein the binder comprises one or more of alginic acid, carboxymethyl cellulose, hyaluronic acid, gelatin, polaxamer, polyvinyl alchol (PVA), polyvinylpyrrolidone (PVP), polylactic acid (PLA), polyglycolide (PG), chitosan, chitin, or an alkali metal salt or an alkaline earth metal salts of any thereof.

9. The method of claim 1, further comprising combining periosteum fibers, fascia fibers, or a combination thereof, with the radiopaque component prior to combining the radiopaque component with the cancellous bone component to form the bone graft material.

10. The method of claim 1, wherein the bone graft material is cryopreserved in a cryopreservative.

11. A bone graft material, comprising:
a radiopaque component; and
a cancellous bone component,
wherein the cancellous bone component comprises native, osteoreparative cells and less than 5% CD4+ cells, less than 5% CD3+ cells, and less than 5% CD45+ cells, and
wherein the radiopaque component comprises particles having an average diameter from 100 microns to 4 mm, and the cancellous bone component comprises a particle size between 1 mm and 4 mm.

12. The bone graft material of claim 11, wherein the radiopaque component comprises non-demineralized cortical bone, barium sulfate, bismuth trioxide, bismuth subcarbonate, tungsten, titanium, zirconium oxide, iodinated polyesters, or iodinated aliphatic monomers.

13. The bone graft material of claim 11, wherein the radiopaque component is non-demineralized cortical bone.

14. The bone graft material of claim 11, wherein the native osteoreparative cells comprise an osteoblast, an osteocyte, an osteoclast, a mesenchymal stem cell, or a combination of any thereof.

15. The bone graft material of claim 11, further comprising a demineralized cortical bone component.

16. The bone graft material of claim 11, wherein the cancellous bone component is a non-enzymatically processed cancellous bone component.

17. The bone graft material of claim 11, further comprising a binder, wherein the binder comprises one or more of alginic acid, carboxymethyl cellulose, hyaluronic acid, gelatin, polaxamer, polyvinyl alchol (PVA), polyvinylpyrrolidone (PVP), polylactic acid (PLA), polyglycolide (PG), chitosan, chitin, or a metal salt of any thereof.

18. The bone graft material of claim 11, further comprising an additive, wherein the additive comprises one or more of a bone morphogenic protein (BMP), fibroblast growth factor-2 (FGF-2), insulin-like growth factor I (IGF-I), insulin-like growth factor II (IGF-II), platelet derived growth factor (PDGF), transforming growth factor beta I (TGFβ-I), or vascular endothelial growth factor (VEGF).

19. The bone graft material of claim 11, further comprising a periosteum fiber, fascia fiber, or combination thereof, wherein the periosteum fiber, fascia fiber, or combination thereof is combined with the radiopaque component prior to formation of the bone graft material.

20. A method of treating a subject with a bone graft material, the method comprising:
administering the bone graft material of claim 11 to the subject,
wherein the bone graft material is administered to the subject to repair a bone defect or bone fracture.

21. The method of claim 4, wherein the cancellous bone component is non-enzymatically processed by passively soaking in cell culture media for up to 60 minutes.

22. The bone graft material of claim 16, wherein the cancellous bone component is non-enzymatically processed by passively soaking in cell culture media for up to 60 minutes.

23. The bone graft material of claim 11, wherein the cancellous bone component comprises 20% to 90% (w/w) of the bone graft material.

24. The bone graft material of claim 11, wherein the radiopaque component comprises 1-20% (w/w) of the bone graft material.

25. The bone graft material of claim 11, comprising greater than 50% CD44+ cells and greater than 30% CD90+ cells.

26. The bone graft material of claim 11, comprising greater than 10% native CD44+ cells adhered to the bone graft material.

27. The bone graft material of claim 11, comprising between 1,000 and 100 million viable cells per gram of bone graft material.

28. The bone graft material of claim 17, wherein the bone graft material comprises hydrated alginic acid, 10% radiopaque component (w/w) and 70% cancellous bone (w/w).

29. The method of claim 20, wherein the bone graft material is administered to the subject during an orthopedic or neurosurgical procedure.

30. The method of claim 29, wherein the orthopedic or neurosurgical procedure is a spinal fusion.

* * * * *